(12) United States Patent
Chambers

(10) Patent No.: US 7,722,629 B2
(45) Date of Patent: May 25, 2010

(54) SYSTEM AND METHOD FOR CATHETER-BASED SEPTAL DEFECT REPAIR

(75) Inventor: Jeffrey W. Chambers, Plymouth, MN (US)

(73) Assignee: Jeffrey W. Chambers, M.D., Maple Grove, MN (US)

( * ) Notice: Subject to any disclaimer, the term of this patent is extended or adjusted under 35 U.S.C. 154(b) by 380 days.

(21) Appl. No.: 10/976,395

(22) Filed: Oct. 29, 2004

(65) Prior Publication Data
US 2006/0095052 A1    May 4, 2006

(51) Int. Cl.
*A61B 17/04* (2006.01)
*A61B 17/12* (2006.01)

(52) U.S. Cl. .................. 606/144; 606/148

(58) Field of Classification Search .............. 606/139, 606/144–150; 128/898
See application file for complete search history.

(56) References Cited

U.S. PATENT DOCUMENTS

| | | | |
|---|---|---|---|
| 5,403,329 A | 4/1995 | Hinchcliffe | |
| 5,571,119 A | 11/1996 | Atala | |
| 5,797,960 A | 8/1998 | Stevens et al. | |
| 5,830,125 A * | 11/1998 | Scribner et al. | 606/139 |
| 5,836,956 A | 11/1998 | Buelna et al. | |
| 5,860,991 A | 1/1999 | Klein et al. | |
| 5,944,738 A | 8/1999 | Amplatz et al. | |
| 6,036,699 A | 3/2000 | Andreas et al. | |
| 6,059,800 A * | 5/2000 | Hart et al. | 606/144 |
| 6,203,554 B1 * | 3/2001 | Roberts | 606/144 |
| 6,290,674 B1 | 9/2001 | Roue et al. | |
| 6,358,258 B1 | 3/2002 | Arcia et al. | |
| 6,551,344 B2 | 4/2003 | Thill | |
| 6,562,052 B2 * | 5/2003 | Nobles et al. | 606/144 |
| 6,679,268 B2 | 1/2004 | Stevens et al. | |
| 2003/0050665 A1 * | 3/2003 | Ginn | 606/215 |
| 2003/0144694 A1 * | 7/2003 | Chanduszko et al. | 606/213 |
| 2004/0006352 A1 | 1/2004 | Nobles et al. | |
| 2005/0251201 A1 * | 11/2005 | Roue et al. | 606/213 |

OTHER PUBLICATIONS

A PCT Search Report (mailed Jul. 17, 2008); 9 pgs.

* cited by examiner

*Primary Examiner*—(Jackie) Tan-Uyen T Ho
*Assistant Examiner*—Melanie Tyson
(74) *Attorney, Agent, or Firm*—Dicke, Billig & Czaja, PLLC

(57) ABSTRACT

The contents include occlusion and/or repair of congenital heart defects including methods, apparatuses, and systems utilizing catheter delivery in order to repair congenital heart defects. In particular, a method of repair includes suturing a septal tissue proximate defect in order to repair the defect with a device introduced through a bodily lumen of a patient. A repair device can include an expansion assembly, a suture delivering portion, and a suture receiving portion.

21 Claims, 16 Drawing Sheets

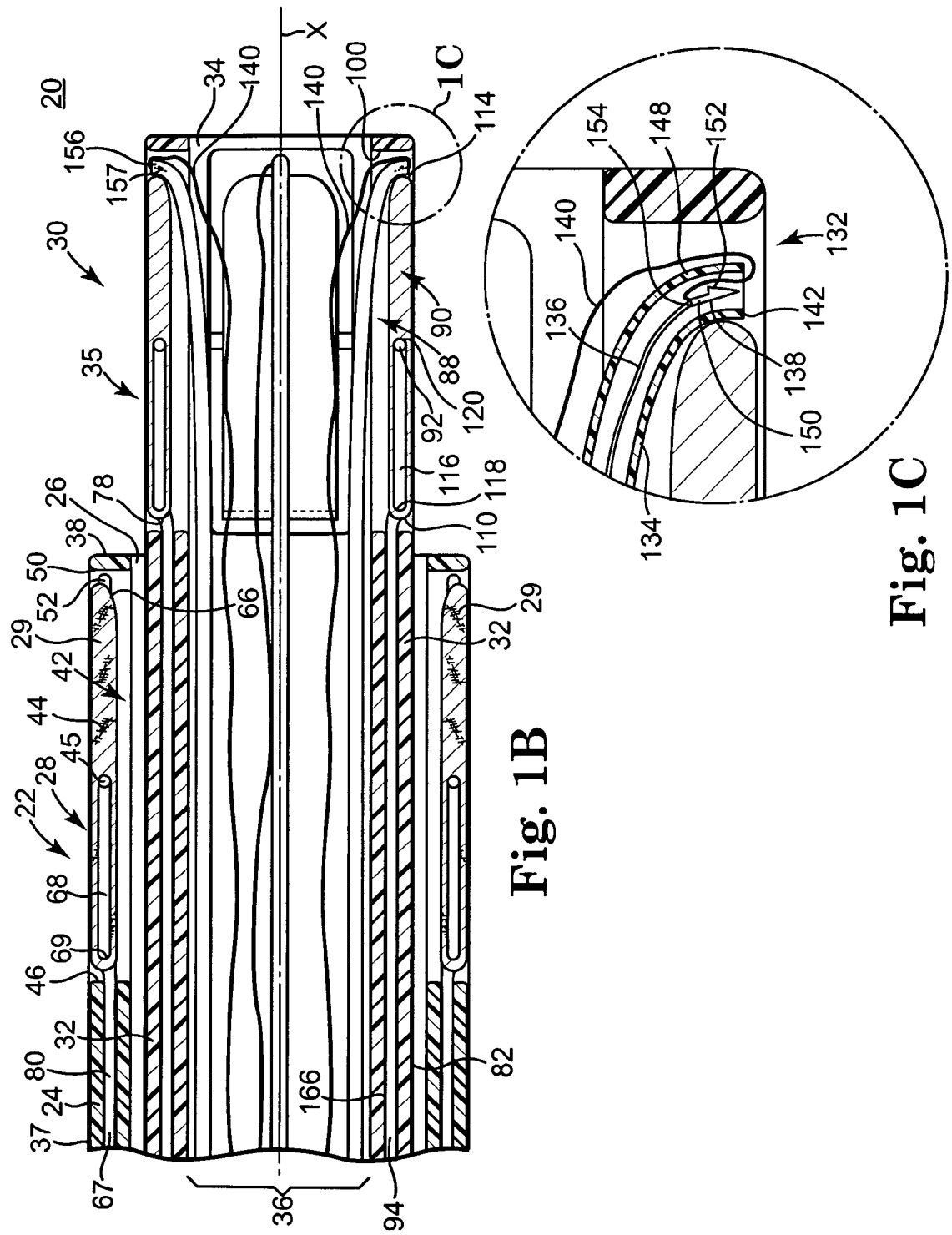

SYSTEM AND METHOD FOR CATHETER-BASED SEPTAL DEFECT REPAIR

FIELD OF THE INVENTION

The present invention relates generally to occlusion and/or repair of defects of the heart. More specifically, the present invention relates to methods, apparatuses and systems utilizing catheter delivery through a bodily lumen of a patient in order to repair congenital heart defects.

BACKGROUND

Congenital heart disease occurs in approximately six to ten children born out of one thousand. In general terms, congenital heart defects are abnormalities in heart structure formation arising during fetal development. While symptoms of such defects may become apparent following childbirth or early childhood, the presence of such defects, and symptoms arising therefrom, may not be recognized until well later into adulthood.

Congenital heart defects include, for example, Atrial Septal Defects (ASDs), Ventricular Septal Defects (VSDs), and Patent Ductus Arteriosis (PDA). Generally speaking, defects in the septum such as ASDs and VSDs are some of the most commonly occurring congenital heart defects. For reference, the septum is composed of muscular tissue and acts to divide the heart into left and right sides. More specifically, the septum includes an atrial septum and a ventricular septum. As the name indicates, ASDs include improper formation of the atrial septum, the wall separating the right atrium and the left atrium. VSDs are generally a hole or other defect in the ventricular septum, the wall separating the right ventricle and the left ventricle. The presence of such congenital heart defects can result in relatively mild symptoms such as decreased energy, shortness of breath, or increased rate of fatigue. However, congenital heart defects can also lead to more serious problems including heart failure, irreversible pulmonary vascular disease, or paradoxic embolization.

One type of ASD is a Patent Foramen Ovale ("PFO"). During fetal development a passageway for blood exists between a septum primum and a septum secundum, which later combine to form the atrial septum. This passage, or opening, is used during fetal development to facilitate blood flow between the two atria in a growing fetus. In non-defective hearts, the opening closes following childbirth due to increased pressure on the left side of the heart. However, in instances where the atrial septum is defective, the passageway remains active after childbirth. This residual opening is a Patent Foramen Ovale. PFOs can be said to act like selective valves in many cases. In operation, the "valve" might only open under certain pressure conditions. For instance, pressure exerted on the heart when a person is sneezing or otherwise straining himself or herself can cause reverse blood flow through a PFO.

In the past, congenital heart defects have largely been treated through open-chest surgery or other invasive procedures requiring access through the chest or torso. Closure, or alternatively occlusion, of some congenital defects has also been accomplished utilizing percutaneous techniques. In particular, a transcatheter approach has been utilized to deliver occlusion devices for ASDs, PDAs, PFOs, and VSDs, for example. Generally, these occlusion devices are delivered to a septal defect and then expanded within the defect in order to both occlude the defect, and anchor the occlusion device in a desired position.

However, the occlusion device technologies mentioned above are potentially hampered by inherent shortcomings. For example, occlusion devices are often limited to use with centrally located defects having both well-defined margins and limited sizes. Furthermore, implantation failures including device migration, embolization, and residual shunts occur at undesirable levels. Indeed, repair of such failures can require emergency open chest surgery. Additionally, holes at the bottom of the atrial septum and large holes in the middle of the atrial septum can be problematic to occlusion device use, and may still require open chest surgery in order to either suture a defect closed, or suture a patch to the defect.

While catheter-based methods can include the shortcomings mentioned above, open chest surgery is still less desirable than less invasive catheter-based methods. In particular, during open chest surgery the heart is normally put under cardioplegic arrest with circulation maintained by cardiopulmonary bypass. The invasiveness of such procedures, as well as stoppage of the heart, drastically increases the risks of death and prolonged recovery. As such, a need exists for methods and associated devices capable of repairing congenital defects via less invasive means, including repairing those defects not amenable to the use of occlusion devices. More specifically, a need exists for a method and apparatus capable of allowing a surgeon to suture a septal defect, or suture a patch to a septal defect, utilizing a catheter delivery method.

SUMMARY

One aspect of the present invention relates to a method of repairing a septal defect in a septum defined by septal tissue. In particular the method includes introducing a guiding catheter into a bodily lumen of a patient and delivering a repair device proximate the septal defect via the guiding catheter. The repair device can include a suture delivering portion maintaining a suture and a suture receiving portion. Opposing sides of the septum are pressed together with the repair device. Further, the suture is positioned at a first location proximate the septal defect with the repair device and driven through the tissue at the first location with the repair device. The suture is positioned at a second location proximate the septal defect and driven through the tissue at the second location with the repair device. Additionally, the suture is captured with the repair device and tied to repair the defect.

Another aspect of the present invention includes positioning a first end of the suture at the first location proximate the septal defect and driving the first end of the suture from a first side of the septum to a second side of the septum with the suture delivering portion of the repair device. The suture is positioned at the second location proximate the septal defect by positioning a second end of the suture at the second location proximate the septal defect. The second end of the suture is driven from the first side of the septum to the second side of the septum with the suture delivering portion. The first and second ends of the suture are captured with the suture receiving portion at the second side of the septum.

Yet another aspect of the present invention includes positioning the suture at the first location with the repair device by positioning a first end of the suture at the first location proximate the septal defect. The suture is driven through the tissue at the first location by driving the first end of the suture from a first side of the septum to a second side of the septum with the suture delivering portion. The first end of the suture is positioned at the second location proximate the septal defect and driven from the second side of the septum to the first side of the septum with the suture delivering portion. The first end of the suture is captured with the suture receiving portion at the first side of the septum and the suture is tied.

Another aspect of the present invention relates to a septal defect repair system for repairing a septal defect in a septum defined by septal tissue. In particular, the system comprises a guide catheter disposed within a bodily lumen of a patient and a repair device disposed within the guide catheter. The repair device includes an expansion assembly configured to press opposing sides of the septum together and a suture delivering portion maintaining a suture and configured to drive an end of the suture through the septal tissue proximate the septal defect. The repair device also includes a suture receiving portion configured to capture the end of the suture from the suture delivering portion.

BRIEF DESCRIPTION OF THE DRAWINGS

The accompanying drawings are included to provide further understanding of the present invention and are incorporated in and constitute a part of this Specification. The drawings illustrate some of the embodiments of the present invention and, together with the description, help explain the principles of the invention. Other embodiments of the present invention and many of the intended advantages of the present invention will be readily appreciated with reference to the Detailed Description when considered in connection with the accompanying drawings.

In the drawings, like reference numerals designate like parts throughout the figures, wherein:

FIG. 1B shows a cross-sectional view along line 1B-1B of FIG. 1A.

FIG. 1C illustrates an enlarged view of the area designated 1C in FIG. 1B.

DETAILED DESCRIPTION

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the figure(s) being described. Because components of embodiments of the present invention can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figure 1A:
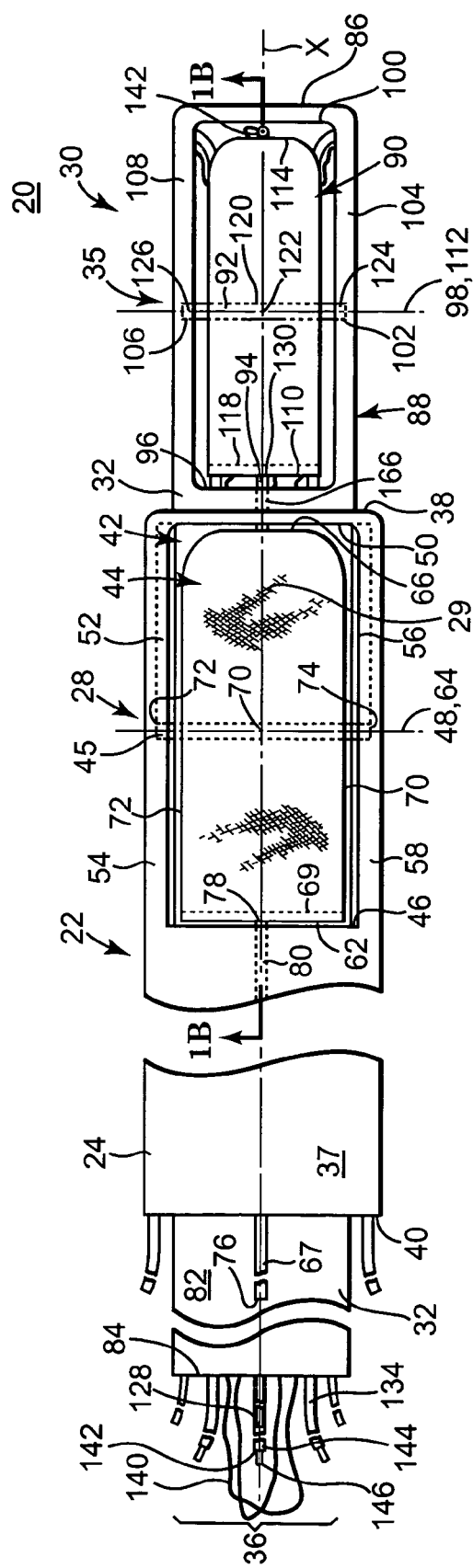
FIG. 1A shows a plan view of an embodiment repair device in accordance with the present invention.

One embodiment of a catheter delivered septal defect repair device 20 in accordance with the present invention is provided in FIGS. 1A and 1B. The repair device 20 is configured for delivery into a body of a patient (not shown) via a catheter introduced into a bodily lumen of the patient, such bodily lumen including veins and/or arteries of the patient (not shown). The repair device 20 defines a central axis X and comprises a first unit 22. The first unit 22 includes a body 24 defining an inner lumen 26 and an expansion assembly 28 defining a suture receiving portion 29 of the repair device 20. In one embodiment, the repair device 20 further comprises a second unit 30. The second unit 30 includes a body 32 defining an inner lumen 34, an expansion assembly 35, and a suture delivering portion 36. In general terms, the repair device 20 can be configured to incorporate a "nested" design in order to facilitate its introduction into a body of a patient (not shown) via catheter insertion. As such, in one embodiment, the first unit 22 is configured for insertion into a catheter and to also accept at least a portion of the second unit 30 within the inner lumen 26 of the first unit 22. With this configuration, for example, both the first unit 22 and the second unit 30 can be concurrently inserted into the body of the patient via subcutaneous methods. However, the operative efficacy of the repair device 20 will be made clearer with reference to the text that follows.

In one embodiment, the first unit body 24 is tubular defining an outer transverse perimeter. They body 24 can be formed of a metallic materials, such as Nitinol®, plastics, or materials similar to those known for use in constructing catheters. The body 24 preferably defines a generally rectangular outer transverse perimeter in cross-section. As such, the body 24 preferably defines four faces 37 (FIG. 2B). However, the body 24 can also define an outer transverse perimeter having other cross-sectional shapes. In one embodiment, the body 24 defines a maximum transverse diameter compatible with insertion into a catheter (not shown). The body 24 also defines a generally rectangular transverse perimeter of the inner lumen 26.

The first unit body 24 extends from a proximal end 40 through a length to a distal end 38. The inner lumen 26 also extends from the proximal end 40 to the distal end 38. Furthermore, and as will be described in greater detail below, the first unit 22 is configured such that the first unit 22 can be manipulated from outside the body of the patient (not shown) to repair a septal defect (not shown). As such, in one embodiment, the body 26 defines a length such that the proximal end 40 can be manipulated from outside the body of the patient while the distal end 38 is located proximate the septal defect. However, it should be understood that the first unit 22 can alternatively incorporate wires or other fixtures extending from the proximal end 40 to allow external maneuvering of the first unit 22 while the distal end 38 of the first unit body 26 is located inside the patient.

In one embodiment, the first unit 22 includes the expansion assembly 28 such that the first unit 22 is capable of being transitioned between an expanded state and a collapsed state. In one embodiment, the expansion assembly 28 includes a plurality of nests 42 formed in the body 24 and a plurality of projections 44, each of the plurality of projections 44 maintained by a corresponding one of the plurality of nests 42. As will be described below, each of the plurality of projections 44 is maintained within a respective one of the plurality of nests 42 with a pin 45 and an actuation wire 67. Although the expansion assembly 28 includes the above-described features, it should be understood that the expansion assembly 28 can also include, springs, balloons, or other expandable structures without departing from the scope of the present invention.

In one embodiment, each one of the plurality of nests 42 is generally rectangular in shape and is formed lengthwise in the body 24. A first one of the plurality of nests 42 defines a proximal end 46, a lengthwise midpoint 48, and a distal end 50. While the first one of the plurality of nests 42 is described in greater detail herein, it is to be understood that a remainder of the plurality of nests 42 can incorporate similar features to those described in association with the first one of the plurality of nests 42. In one embodiment, each one of the plurality of nests 42 is preferably disposed radially about the body 24. As such, one embodiment includes four nests 42, each of the four nests 42 formed in a respective one of the faces 37 of the body 24. As shown, each one of the plurality of nests 42 is formed through a thickness of the body 24. However, it is to be understood that in other embodiments, each one of the plurality of nests 42 can be formed partially through the thickness of the body 24.

Each of the plurality of nests 42 includes a first pin track 52 (shown with dotted lines in FIG. 1A and shown partially covered in FIG. 1B) formed in the thickness of the body 24 and extending along a nest first side 54 from the lengthwise midpoint 48 to the distal end 50. A corresponding second pin track 56 (shown with dotted lines in FIG. 1A) is also formed in the thickness of the body 24, extending along an opposing nest second side 58 from the lengthwise midpoint 48 to the distal end 50. In other words, in one embodiment, each of the plurality of nests 42 includes an opposing pair of pin tracks 52,56 extending along opposing nest sides 54,58. As will be described in greater detail below, the two pin tracks 52,56 are configured to slidably maintain the pin 45. The two pin tracks 52,56 can also be configured to rotatably maintain the pin 45.

In one embodiment, each of the plurality of projections 44 defines a proximal end 62, a lengthwise midpoint 64, and a distal end 66. In one embodiment, each of the plurality of projections 44 is configured such that an actuation wire 67 can be affixed to the proximal end 62.

The plurality of projections 44 can be generally similar in size to the corresponding nests 42. As such, in one embodiment, each of the plurality of projections 44 is a generally rectangular and flat petal. However, each of the plurality of projections 44 is not as wide or as long as the nest 42 in which it is maintained. In this manner, the plurality of projections 44 can be maintained in the corresponding one of the nests 42 without interfering with either of the opposing sides 54,58 or proximal and distal ends 46,50. Furthermore, each of the plurality of projections 44 is configured to be maintained within the corresponding nest 42 without protruding from the outer transverse perimeter of the body 24 when the first unit 22 is in the collapsed state.

As shown in FIGS. 1A and 1B, each of the plurality of projections 44 forms a pin slot 68 configured to accept the pin 45. In one embodiment, the pin slot 68 originates at a proximal end 69 proximate the proximal end 62 of the projection 44 and extends proximate to the lengthwise midpoint 64. As shown by the dotted lines in FIG. 1B, the pin slot 68 extends widthwise entirely from a first side 70 to an opposing second side 72 through a thickness of the projection 44. In this manner, the pin 45 can be slidably retained within the pin slot 62 while remaining partially exposed from the opposing sides 70,72 of the projection 44.

In one embodiment, the first unit 22 defines, or includes, the suture receiving portion 29 of the repair device 20. The suture receiving portion 29 can be generally described as a suture needle retaining structure. As shown in FIGS. 1A and 1B, each of the plurality of projections 44 can define at least part of the suture receiving portion 29. In one embodiment, the suture receiving portion 29 includes a conical receptacle that is generally complementary in shape to a suture needle with a porous material at a base of the conical receptacle (not shown). Additionally, it should be understood that other materials that can promote frictional engagement of a suture and/or suture material (not shown) could also be employed. In another embodiment, and as shown in FIGS. 1A and 1B, the suture receiving portion 29 is defined by at least a portion of the plurality of projections 44 being formed of a mesh material suitable for capturing a suture. In an exemplary embodiment, the plurality of projections 44 are formed of Nitinol® wire-mesh material. However, alternative suture receiving portions 29 can be incorporated by the first unit 22 and defined by the plurality of projections 44. For example, the suture receiving portion 29 can include forming at least a portion of the plurality of projections 44 of a relatively soft material. In other embodiments, the suture receiving portion 29 can also include detents, magnets, adhesives, locking mechanisms or other features suited to suture needle capture. It will be understood with reference to the text that follows that the second unit 30 can also define, or include, a suture receiving portion of the repair device 20.

In one embodiment, the pin 45 defines a pin central portion 70, a pin first end 72, and an opposing pin second end 74. The pin 45 can be a solid rod formed of a material such as Nitinol®. As shown in FIG. 1B, the pin 45 defines a generally circular transverse cross-section. In alternative embodiments, the pin 45 can also define a cam shape in transverse cross-section.

In one embodiment, the actuation wire 67 is adapted to be affixed to the proximal end 46 of the corresponding projection 44. Furthermore, the actuation wire 67 preferably defines a length such that a proximal end 76 of the actuation wire 67 can be manipulated from a point outside of the body of the patient (not shown) while a distal end 78 of the actuation wire 67 is affixed to the corresponding projection 44. The actuation wire 67 can be formed of a variety of materials, but in one embodiment is formed of Nitinol® wire. As will become more evident below, the actuation wire 67 is configured such that an operator (not shown) manipulating the proximal end 76 of the actuation wire 67 can push and/or pull the wire in order to transition the first unit 22 between the expanded and the collapsed states.

The repair device 20 is shown in FIGS. 1A and 1B with the first unit 22 in a collapsed state. The plurality of projections 44 and the plurality of nests 42 are preferably assembled together to define the collapsed state shown in FIGS. 1A and 1B as follows. The plurality of projections 44 are maintained within corresponding ones of the plurality of nests 42 such that the plurality of projections 44 do not protrude, or extend outwardly from, the corresponding nest 42. In other words, the plurality of projections 44 generally lie "in plane" with the corresponding nests 42 and a surrounding portion of the body 24.

As alluded to above, the pin 45 acts to help maintain the projection 44 in the corresponding nest 42, as the central portion 70 of the pin 45 is slidably maintained in the pin slot 68. Further, the pin first end 72 is slidably maintained in the first pin track 52 and the pin second end 74 is slidably maintained in the second pin track 56. With this arrangement, the pin 45 can be slid within both the pin slot 68 and the opposing pin tracks 52,56. Further, the pin slot 68, the opposing pin tracks 52,56, or both, can be configured to allow the pin 45 to rotate. As will be described below, such a configuration allows the projection 44 to be moved distally within the corresponding nest 42 in which it resides, while also allowing the distal end 66 of the projection 44 to rotate outward away from the body 24 to the position shown in FIGS. 2A and 2B.

Additionally, it is to be understood that tension on the actuation wire 67 aids in maintaining the corresponding projection 44 "in plane" as shown. In one embodiment, the actuation wire 67 extends through a channel 80 formed through the thickness of the body 24. In particular, the actuation wire 67 extends proximally beyond the body proximal end 40. However, the actuation wire 67 can alternatively take an external path to the body 36 to extend beyond the body proximal end 40. Further, the actuation wire 67 can also extend over an internal path, e.g., within the inner lumen 26, to extend beyond the body proximal end 40. In one embodiment, the actuation wire 67 extends a sufficient length such that an operator (not shown) is capable of manipulating the actuation wire proximal end 76 from outside the body of the patient (not shown).

With reference from FIGS. 1A and 1B to FIGS. 2A and 2B, a manner of transitioning the first unit 22 from the collapsed state (FIGS. 1A and 1B) to the expanded state (FIGS. 2A and 2B) follows. In particular, the actuation wire 67 is moved forward, or distally, resulting in the corresponding projection 44 sliding distally over the pin 45 associated therewith. In one embodiment, the distal end 66 of the projection 44 is configured such that it is guided by a distal end 50 of the corresponding nest 42 outward from the central longitudinal axis X. In this manner, the projection 44 will also rotate about the pin 45. In one embodiment, the actuation wire 67 is affixed to the proximal end 62 of the corresponding projection 44. As shown in FIG. 1B, the actuation wire 67 can be affixed to the proximal end 62 at an offset in order to facilitate the outward extension, or deflection of the projection distal end 66. In other words, distal movement of the actuation wire 67 can be partially directed toward the central longitudinal axis X by the offset in order to push the proximal end 62 of the corresponding projection 44 inward towards the central longitudinal axis X. As shown, the distal end 66 of the projection 44 then deflects, or projects, outward from a central longitudinal axis X of the first unit body 24.

As the projection 44 slides distally and rotates outwardly, the pin 45 eventually reaches the proximal end 69 of the pin slot 68. In one embodiment, the projection 44 extends at a perpendicular angle to the central longitudinal axis X when the pin 45 has reached the pin slot proximal end 69. The continued distal actuation, or pushing, of the actuation wire 67 can then result in further distal movement of the projection 44. In particular, the pin 45 will slide distally within the two opposing pin tracks 52,54. Additionally, in one embodiment, the pin 45 will slide in this manner after the projection 44 has been extended perpendicularly to the central longitudinal axis X.

Additional means of accomplishing this perpendicularly extended and distal actuation will be recognized by those of ordinary skill in the art. For example, in one embodiment, this type of actuation is partially accomplished by the pin 45 defining a cam capable of interacting with the pin tracks 52,54, or alternatively the pin slot 68. However, cam structures are simply one means of causing the plurality of projections 44 to arrest rotation at a perpendicular position relative to the central longitudinal axis X. For example, those having ordinary skill in the art will recognize that stops, additional linkages, or other features can also be implemented to accomplish such movement.

Figure 2A:
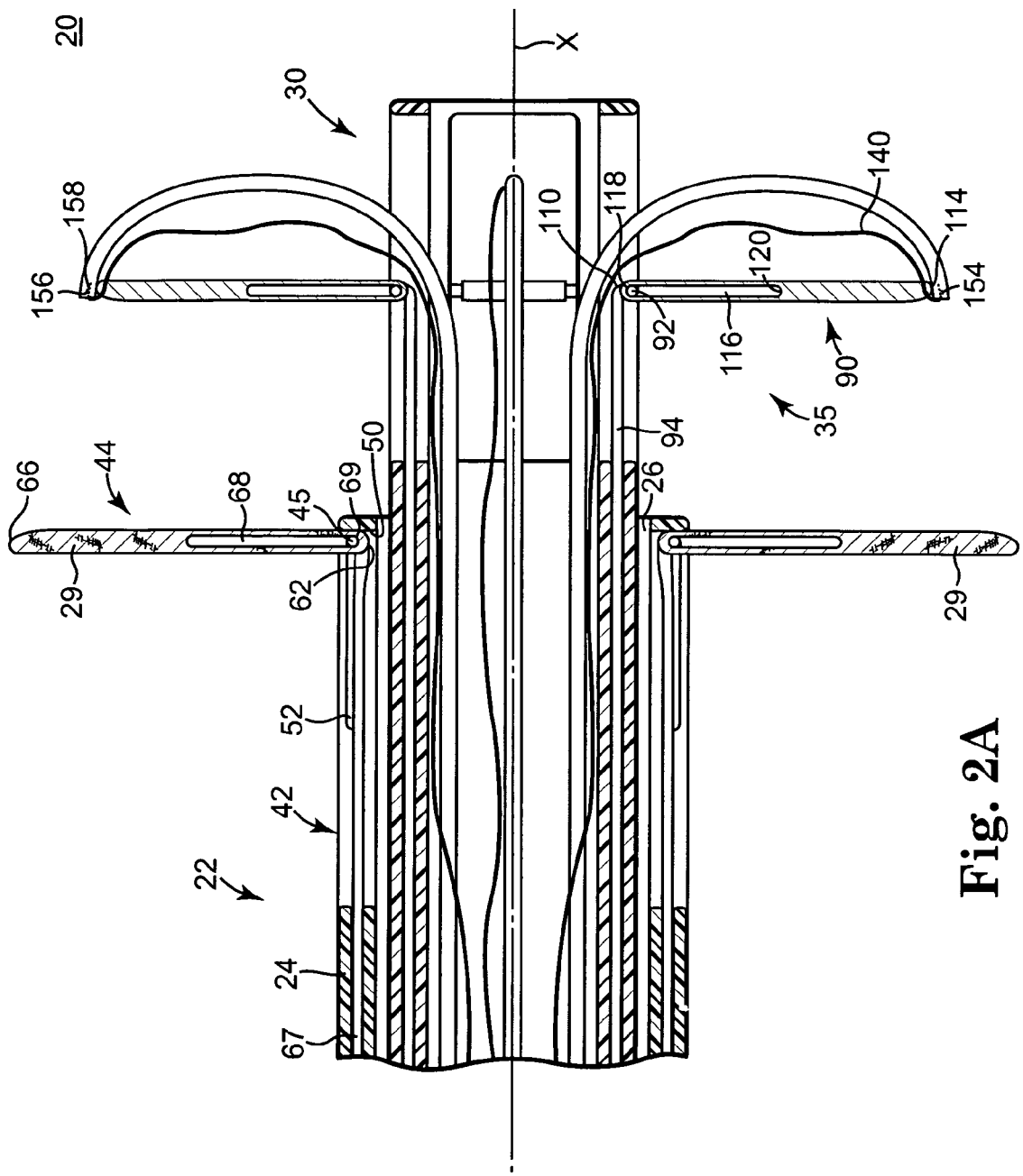
FIG. 2A is a cross-sectional view of the repair device of FIG. 1A similar to that of FIG. 1B, with first and second units in an expanded state.
Figure 2B:
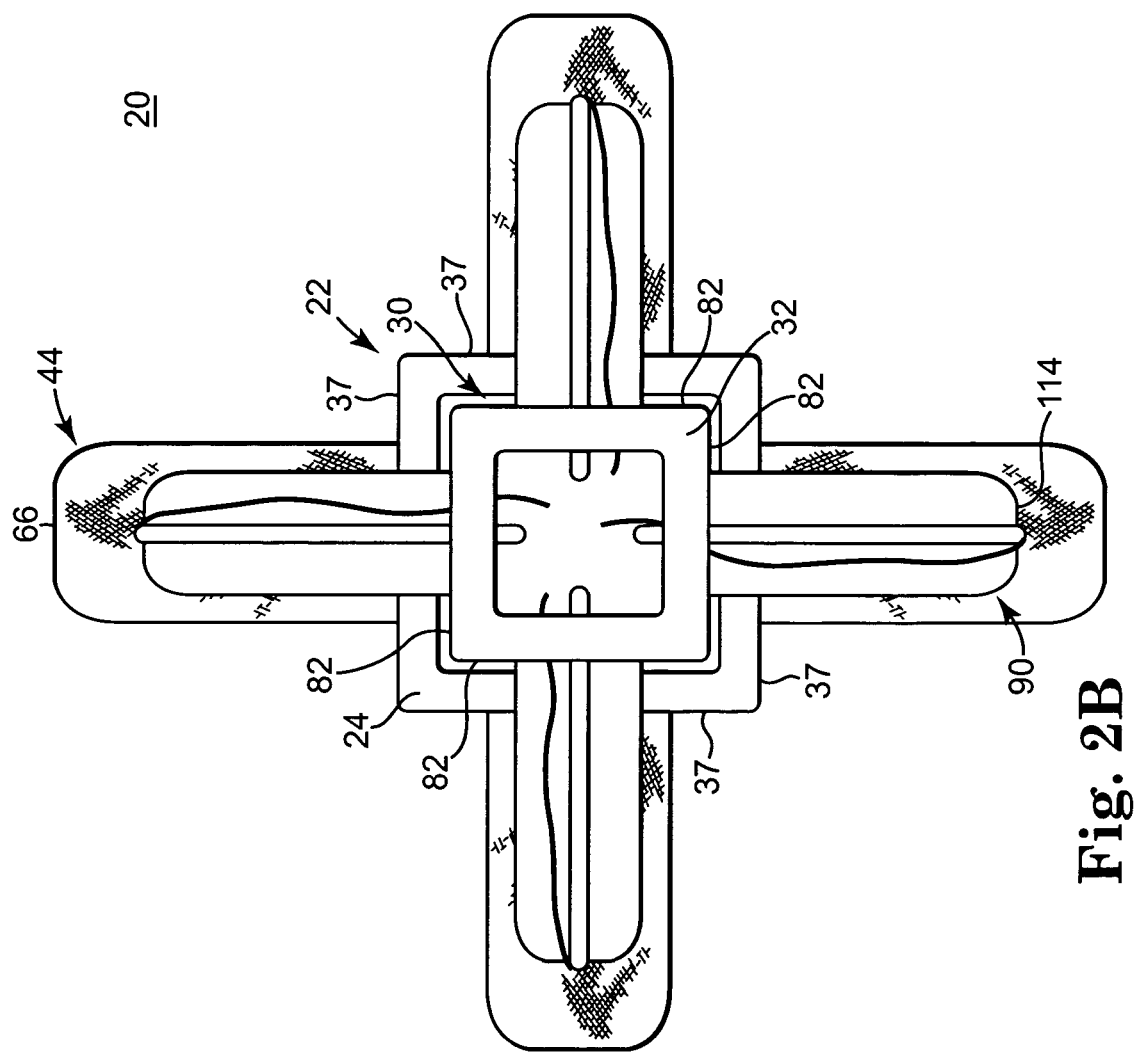
FIG. 2B illustrates an end view of the repair device of FIG. 1A, with the first and second units in an expanded state.
Figure 3:
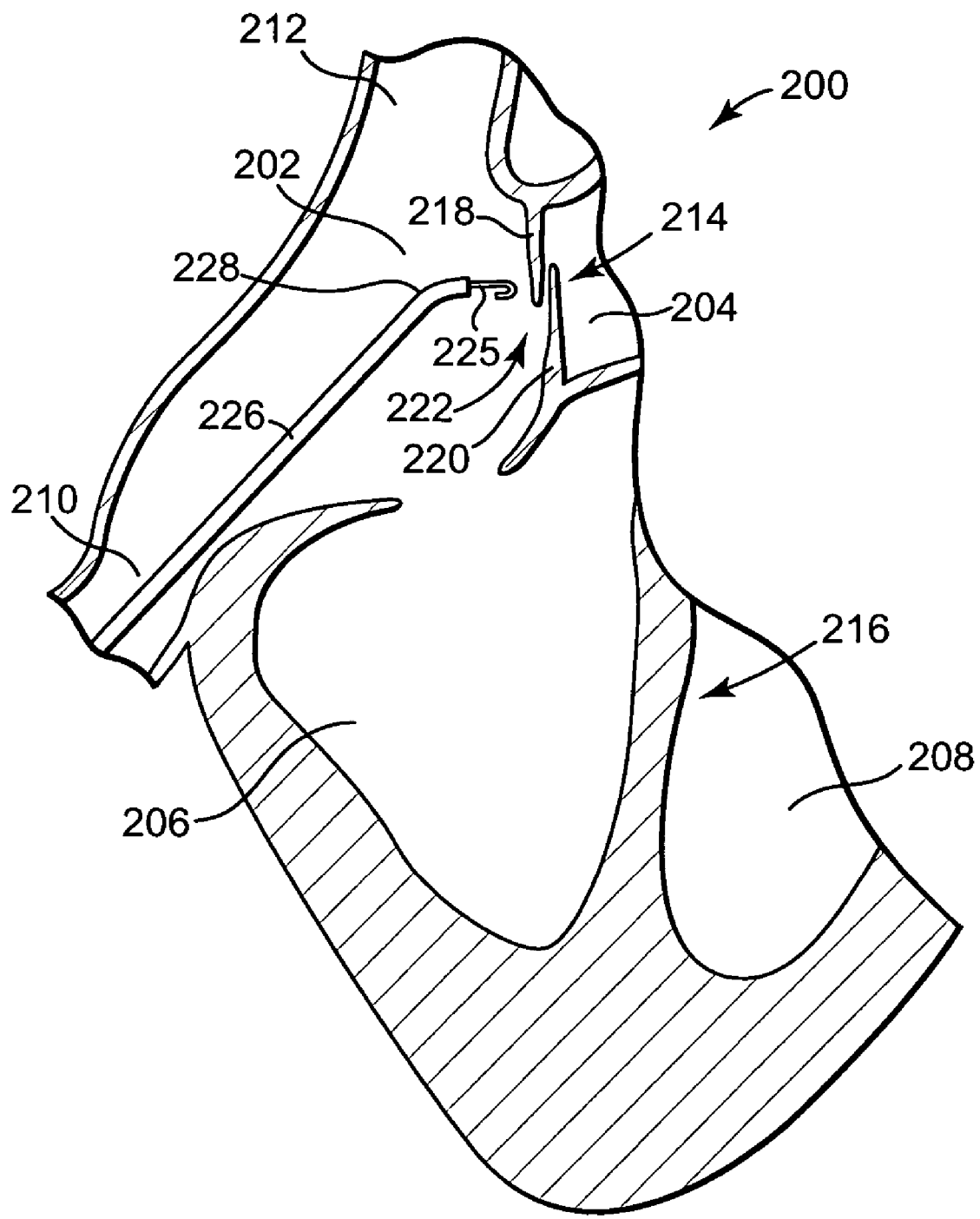
FIGS. 3 to 12B illustrate a method of repairing a septal defect in accordance with the present invention.

The plurality of projections 44 will preferably take the position shown in FIGS. 2A and 2B once the corresponding pins 45, and consequently, the plurality of projections 44, have been slid to the distal end 50 of the corresponding nests 42. In this position, a proximal portion of the plurality of projections 44 will preferably abut against a portion of the first unit body 24 defining the nest distal end 50. Distal actuation, or pushing, of the corresponding actuation wires 67 will preferably act to support the projections 44 in this perpendicularly extended position, while also maintaining the projections 44 at the distal end 50 of the respective nests 42.

It should also be recognized that the first unit 22 can be collapsed, or transitioned from the expanded to the collapsed state shown in FIGS. 1A and 1B. In particular, transitioning the first unit 22 from the expanded state to the collapsed state includes proximal actuation, or pulling, of the actuation wires 67 to effectuate a reverse series of events to those described in association with expansion of the first unit 22. In other words, expanding the first unit 22 includes pushing on the actuation wires 67, while collapsing the first unit 22 includes pulling on the actuation wires 67. However, those of ordinary skill in the art will recognize that alternative means of either expanding, or collapsing the first unit 22, and in particular, actuation of the plurality of projections 44, can be employed. For instance, in alternative embodiments, spring mechanisms can be included in the first unit 22 in order to facilitate expanding or collapsing the first unit 22.

Returning to FIGS. 1A and 1B, and turning now to the second unit 30, the second unit body 32 is tubular defining an outer transverse perimeter in one embodiment. Generally, the second unit body 32 can be formed with similar materials to those forming the first unit body 24. In one embodiment, the second unit body 32 defines a generally rectangular outer transverse perimeter in cross-section having a shape factor similar to that of the outer transverse perimeter of the first unit body 24. Additionally, the second unit body 32 defines a maximum outer transverse diameter such that the second unit body 32 can be disposed within the inner lumen 26 defined by the first unit body 24. With the embodiment having a rectangular cross-section, the second unit body 32 defines four faces 82 corresponding to the rectangular outer transverse perimeter. However, the body 32 can define other cross-sectional shapes with the outer transverse perimeter. In one embodiment, the body 32 also defines a generally rectangular transverse perimeter of the inner lumen 34. The second unit body 32 extends from a proximal end 84 through a length to a distal end 86. Further, the inner lumen 34 extends from the proximal end 84 to the distal end 86.

As will be described in greater detail below, the second unit 30 is also configured to be manipulated from outside the body of the patient to repair the septal defect in the body of the patient (not shown). As such, in one embodiment, the body 32 defines a length such that the proximal end 84 can be manipulated from outside the patient while the distal end 86 is located proximate the septal defect. However, as with the first unit 22, it should be noted that the second unit 30 could alternatively incorporate additional wires or other fixtures extending from the body 32 which allow external maneuvering of the second unit 30 while the distal end 86 of the second unit body 32 is located inside the patient.

In one embodiment, the second unit 30 includes the expansion assembly 35 such that the second unit 30 is also capable of transitioning between an expanded state and a collapsed state. In one embodiment, the expansion assembly 35 includes a plurality of pockets 88 formed in the second unit body 32 and a plurality of guide bodies 90, each one of the plurality of guide bodies 90 maintained by a corresponding one of the plurality of pockets 88. In one embodiment, each of the plurality of guide bodies 90 is maintained in a corresponding pocket 88 with a pin 92 and actuated with an actuation wire 94. Although embodiment expansion assemblies have been described as including the structures mentioned above, it should be understood that the expansion assembly 28 could include alternative structures such as balloons, springs, or other expandable structures without departing from the scope of the present invention.

While one of the plurality of pockets 88 is described below in greater detail, it is to be understood that all of the pockets 88 can incorporate similar features. As shown in FIG. 1A, the pocket 88 is generally rectangular in shape and is formed lengthwise in the second unit body 32. The pocket 88 defines a proximal end 96, a lengthwise midpoint 98, and a distal end 100. Similarly to the first unit 22, the plurality of pockets 88 are disposed radially about the second unit body 32. In particular, one embodiment includes four pockets 88, each formed in a respective one of the faces 82 of the body 32. As shown, each of the pockets 88 is formed through a thickness of the body 32. However, as with the first unit 22, it is to be understood that in alternative embodiments, the pockets 88 can be formed partially through the thickness of the body 32.

As shown in dotted lines in FIG. 1A, the pocket 88 includes a first female pin mount 102 formed in the thickness of the body 32. In particular, the first female pin mount 102 is formed at the lengthwise midpoint 98 in a first side 104 of the pocket 88. A corresponding second female pin mount 106 is formed in an opposing second side 108. In particular, the second female pin mount 106 is formed in the thickness of the body 32 at the lengthwise midpoint 98 of the pocket 88. As will be described in greater detail below, the pin 92 is rotatably maintained within the two female pin mounts 102,106. In another embodiment, the pockets 88 can incorporate structures similar to those described in association with the first unit 22, including opposing pin tracks for maintaining the pin 92.

While one of the plurality of guide bodies 90 is described in greater detail below, it is to be understood that each of the plurality of guide bodies 90 can incorporate similar features. With that in mind, the guide body 90 defines a proximal end 110, a lengthwise midpoint 112, and a distal end 114. Additionally, guide body 90 can define a similar shape factor to the corresponding pocket 88. However, it is to be understood that the guide body 90 can include tapers or rounds, such as the taper toward the distal end 114 as shown in FIG. 1A. In one embodiment, the guide body 90 is a generally rectangular and flat petal. In one embodiment, the guide body 90 is not as wide or as long as the corresponding pocket 88. In particular, the guide body 90 is configured for reception within the corresponding pocket 88 without interfering with either of the opposing sides 104,108 or the proximal and distal ends 96,100 of the pocket 88.

In one embodiment, the guide bodies 90 are configured to be maintained "in plane" within the respective pocket 88, without protruding from the outer transverse perimeter of the body 32 when the second unit 30 is in the collapsed state. Furthermore, when expanded, the guide bodies 90 are configured to extend from the central axis X less than the plurality of projections 44 of the first unit 22 in the expanded state. As will be understood with reference to the description below, this relative sizing can facilitate suture needle capture in the suture receiving portion 29 of the first unit 22. Along these lines, in one embodiment, the guide bodies 90 are formed of a solid material that can be resistant to suture needle penetration. In another embodiment, at least a portion of the guide bodies 90 defines the suture receiving portion 29 of the repair device 20.

As shown in FIGS. 1A and 1B, the guide body 90 forms a pin slot 116 configured to accept the pin 92. In one embodiment, the pin slot 116 originates at a proximal end 118 proximate the proximal end 110 of the guide body 90 and extends within a thickness of the guide body 90 to a slot distal end 120 proximate the lengthwise midpoint 112. As shown in FIG. 1B, the pin slot proximal end 118 begins distal to the proximal end 114 such that the pin 92 can be maintained within the thickness of the pin slot 116 as it slides between the proximal and distal ends 118,120 of the pin slot 116.

In one embodiment, the pin 92 is a solid rod formed of a material such as Nitinol®. In a related embodiment, the pin 92 defines a generally circular cross-section and defines a pin central portion 122, a pin first end 124, and a pin second end 126. In alternative embodiments, the pin 92 defines a cam shape in transverse cross-section.

In one embodiment, the actuation wire 94 is configured for fixation to the proximal end 110 of the corresponding guide body 90. The actuation wire 94 defines a length such that an actuation wire proximal end 128 can be manipulated from a point outside of the body of the patient (not shown) while an actuation wire distal end 130 is affixed to the corresponding guide body 90. The actuation wire 94 can be formed of a variety of materials, but in one embodiment, is formed of Nitinol® wire.

The suture delivering portion 36 can be described in greater detail with reference to FIGS. 1A, 1B, and 1C. In one embodiment, the suture delivering portion 36 includes a plurality of push member assemblies 132. In an exemplary embodiment, the number of push member assemblies 132 corresponds to the number of guide bodies 90 of the expansion assembly 36. With reference to FIG. 1C, each of the push the member assemblies 132 includes a needle catheter 134, a push member 136 disposed within the needle catheter 134, a needle 138 removably affixed to the push member 136, and a suture 140 affixed to the needle 138. While one of the push member assemblies 132 is described in greater detail below, it is to be understood that each of the plurality of push member assemblies 132 can incorporate similar features.

With reference to FIG. 1A, in one embodiment, the needle catheter 134 defines a proximal end 142 and extends a length to define a distal end 144. The needle catheter 134 can be of a type similar to those generally known in the art. The length of the needle catheter 134 extends sufficiently such that the proximal end 142 of the needle catheter 134 can be manipulated from outside the body of a patient (not shown) while the catheter distal end 142 is affixed to the distal end 114 of the first one of the plurality of projections 90. Manners of affixing the distal end 142 to the distal end 114 include such techniques as sonic or laser welding, for example. In one embodiment, the outer diameter of the needle catheter 134 is such that a plurality of needle catheters included in the plurality of push member assemblies 132 and similar to the needle catheter 134, can be disposed within the inner lumen 34 of the second unit body 32. The inner diameter of the needle catheter 134 is preferably such that the push member 136 can be disposed within the needle catheter 134.

In one embodiment, the push member 136 defines a proximal end 146 and extends a length to a distal end 148. As mentioned above, the push member 136 is disposed within the needle catheter 134. As described in greater detail below, the length of the push member 136 preferably extends sufficiently such that a proximal end 146 of the push member 136 extends from the catheter proximal end 142 and can be manipulated from outside of the patient (not shown), while the distal end 148 of the push member 136 extends from the catheter distal end 144. The push member 136 is made of a material such as Nitinol® wire, or plastic, for example. In particular, the push member 136 is preferably configured such that an operator (not shown) can impart a push force on the push member proximal end 146 with a resultant push force being translated to the push member distal end 148.

With reference again to FIG. 1C, in one embodiment, the needle 138 includes a base 150 configured to be removably affixed to the push member distal end 148. This relationship can be accomplished via means generally known in the art, including interference fits, semi-permanent glues, operatively breakable welds, magnets, actuated clips, operatively breakable lashes, and others. Further, the needle 138 is configured for affixment to the suture 140. In one embodiment, the needle 138 also includes a barb 152. In particular, the barb 152 can be configured to aid in capturing the needle 138 with the suture receiving portion 29 of the first unit 22.

In one embodiment, the suture 140 extends continuously from a first end 154 to a second end 156 (FIG. 2A). As described above, the first end 154 is preferably adapted to be affixed to the needle 138. In one embodiment, the second end 156 is affixed to a needle 157 (shown in dotted lines in FIG. 2A) of another one of the plurality of push member assemblies 132.

In one embodiment, the suture delivering portion 36 defines a non-extended state, including the needle 138 residing within the needle catheter 134 proximate the needle catheter distal end 144. The push member 136 can then be moved distally from outside the body of the patient (not shown) to transition to the suture delivering portion 36 to an extended state such that the needle 138 extends from the needle catheter distal end 144 sufficiently to drive the needle 138 through the septum as desired (not shown).

The repair device 20 is shown in FIGS. 1A and 1B with the second unit 30 in the collapsed state. The plurality of guide bodies 90 and the plurality of pockets 88 are preferably assembled together to define the collapsed state as follows. Each of the plurality of guide bodies 90 is maintained within a corresponding one of the plurality of pockets 88 such that the plurality of guide bodies 90 do not protrude, or extend outwardly from the corresponding pockets 88. In other words, the plurality of guide bodies 90 generally lie "in plane" with the corresponding pocket 88 and a surrounding portion of the second unit body 32.

As alluded to above, the pin 92 acts to help maintain the corresponding guide body 90 within the respective pocket 88. In particular, the pin central portion 122 is rotatably and slidably maintained in the pin slot 116 while the pin ends 124,126 are maintained in the female pin mounts 102,106. With this arrangement, the pin 92 can be slid within the pin slot 116 and rotated about the pin 92. Further, the female pin mounts 102,106 can also be configured to allow the pin ends 124,126 to rotate within them. As will be described in greater detail below, rotation of the guide body 90 about the pin 92 can facilitate extension of the distal end 114 of the guide body 90 from the corresponding pocket 88 in a manner somewhat similar to that described in association with the first unit 22.

In one embodiment, the actuation wires 94 extend through a corresponding channel 166 formed through the thickness of the second unit body 32. In particular, each actuation wire 94 preferably extends proximally beyond the body proximal end 84. However, each actuation wire 94 can alternatively take an external path to the body 32 to extend beyond the body proximal end 84. Further, each actuation wire 94 can also extend over an internal path, e.g., within the inner lumen 34, to extend beyond the body proximal end 84. In one embodiment, the actuation wire proximal end 128 extends a sufficient length such that an operator (not shown) is capable of manipulating the actuation wire proximal end 128 from outside the patient (not shown). As described below, pulling or proximal force on the actuation wire 94 can act to maintain the corresponding guide body 90 "in plane" as shown in FIGS. 1A and 1B, while pushing or distal force on the actuation wire 94 acts to extend the corresponding guide body 90 "out of plane."

As mentioned above, each of the plurality of push member assemblies 132 can be affixed to the corresponding distal end 114 of a respective one of the plurality of guide bodies 90. More specifically, the distal end 44 of the needle catheter 134 is affixed to the distal end 114 such that the lumen of the needle catheter 134 is arranged perpendicularly to the length of the corresponding guide body 90. In this manner, the lumen of the needle catheter 134 can be directed toward a septum (not shown) when the second unit 30 is in the expanded state. Means of affixing the needle catheter 134 to the corresponding guide body 90 can include those generally known in the art, including, but not limited to, welds, glues, magnets, lashes, clamps, and others.

With reference from FIGS. 1A and 1B to FIGS. 2A and 2B, a manner of expanding the second unit 30 from the collapsed state (FIGS. 1A and 1B) to the expanded state (FIGS. 2A and 2B) follows. In particular, pushing, or distal movement of the actuation wires 94 preferably results in the plurality of guide bodies 90 sliding distally on the corresponding pin slot 116 over the respective pin 92. In one embodiment, the distal end 110 of the each of the plurality of guide bodies 90 is configured such that it is guided by the distal end 100 of the corresponding pocket 88 outward from the central longitudinal axis X as it is moved distally by the corresponding actuation wire 94. In this manner, each of the plurality of guide bodies 90 will preferably also rotate about the corresponding pin 92 as it moves distally. In one embodiment, the actuation wires 94 are connected to the proximal end 110 of the corresponding guide body 90 at an offset toward the central longitudinal axis X. In the embodiment, this configuration aids in directing the proximal end 110 toward the longitudinal axis X, resulting in direction of the distal end 114 outward, away from the longitudinal axis X in a sliding "see-saw" manner.

As the guide body 90 slides distally and the distal end 114 rotates outwardly, the pin 92 eventually reaches the proximal end 118 of the pin slot 116. Once the proximal end 118 has been reached, the guide body 90 extends at a perpendicular angle to the central longitudinal axis X. In light of the description provided herein, means of accomplishing this perpendicular extension via distal actuation, or pushing, will be recognized by those having ordinary skill in the art. For example, one such means includes incorporation of a cam structure into the pin 92 configured to interact with the female pin mounts 102,106 and/or the pin slot 116. A manner of retaining the guide bodies 90 in the perpendicular position shown includes maintaining the actuation wire 94 in a fixed position after the corresponding guide body 90 has been extended.

Similarly to the first unit 22, it should also be recognized that the second unit 30 can be collapsed, or transitioned from the expanded state to the collapsed state shown in FIGS. 1A and 1B. In particular, transitioning the second unit 30 from the expanded state to the collapsed state can include proximal actuation, or pulling, of the actuation wires 94 to effectuate a reverse series of motions to those described in association with expansion of the second member 30. In other words, expanding the second unit 30 includes pushing on the actuation wires 94, while collapsing the second unit 30 includes pulling on the actuation wires 94. However, those of ordinary skill in the art will recognize that alternative means of either expanding, or collapsing the second unit 30, and in particular, actuation of the plurality of guide bodies 90, can be employed. For instance, in alternative embodiments, spring mechanisms or balloons can be included in the second unit 30 in order to facilitate expanding or the collapsing the second unit 30.

As mentioned above, the first and second units 22,30 are configured for catheter insertion into the body of the patient (not shown). Generally, the first unit 22 is slidably disposed about the second unit 30. More specifically, the first unit body 24 is slidably disposed about the second unit body 32, such that the second unit 30 can be extended from the first unit body 24 but cannot be rotated therein. In one embodiment, an operator (not shown) manipulates the first unit body proximal end 40 and the second unit body proximal end 84 from outside the body of the patient (not shown) to effectuate relative extension. With this configuration, the suture delivering portion 36 of the second unit 30 can be extended while remaining aligned with the suture receiving portion 29 of the first unit 22. For example, and as shown in FIGS. 1A, 1B, 2A and 2B, the non-rotatable configuration allows both units 22,30 to be transitioned to the expanded state with the second unit plurality of guide bodies 90 aligned with the first unit plurality of projections 44.

As such, the second unit 30 is extended from the first unit inner lumen 26 prior to transitioning to the expanded state in the manner described above. As will be described in greater detail below, this slidable and nested configuration also allows the repair device 20 to reside on two sides of a septal defect (not shown) in order to opposingly anchor the structures surrounding the septal defect between the two units 22,30.

Additionally, the first unit 22 can alternatively be configured to be disposed within the second unit 30. Indeed, it is to be understood that in embodiments of the present invention, the features described in association with the first and second units are interchangeable. For example, the first unit 22 can include the suture delivering portion 36 while the second unit 30 includes the suture receiving portion 29.

With that in mind, and with reference to FIGS. 3-12B, a system and method of repairing a congenitally defective heart 200 can be described. For those not familiar with the nomenclature commonly associated with cardiac structures, the designation "left" or "right" corresponds to the "left" and "right" of the patient (not shown) and should be interpreted accordingly. The heart 200 is shown from a front of the patient (not shown) and generally includes a right atrium 202, a left atrium 204, a right ventricle 206, and a left ventricle 208. An inferior vena cava 210 and a superior vena cava 212 also lead into the right atrium 202. A septum divides the heart 200 into a right half and a left half. More specifically, the septum includes an atrial septum 214 and a ventricular septum 216. The atrial septum 214 separates the right and left atria 202,204 while the ventricular septum 216 separates the right and left ventricles 206,208.

The atrial septum 214 is formed by septal tissue and includes a septum primum 218 and a septum secundum 220. Prior to childbirth the septum primum 218 and the septum secundum 220 define a passageway for blood between the right and left atria 202,204 Following childbirth, the passageway will close in a healthy heart (not shown). As shown, the heart 200 includes a septal defect 222 in the form of such a passageway, a patent foramen ovale. In one embodiment, the patent foramen ovale occurs due to improper formation of the septum primum 218. In other embodiments, the patent foramen ovale occurs due to improper formation of the septum secundum 220, or both the septum primum 218 and the septum secundum 220.

Furthermore, while embodiment methods of repairing a congenital heart defect will be described in association with the septal defect 222 including the patent foramen ovale, it is to be understood that the principles and embodiments described herein can be applied to other types of congenital heart defects, including, for example, ventricular septal defects.

In one embodiment, a guide wire 225 is introduced into the body of the patient (not shown) via a sheath in the femoral artery (not shown). The guide wire 225 is introduced into the heart 200 in a manner known in the art. In one embodiment, the guide wire 225 is a J-Tip wire. A guide catheter 226 is then threaded over the guide wire 225 and into the heart 200. Generally, the guide catheter 226 will be introduced into one or more bodily lumens and delivered to the heart 200. In one embodiment, a distal portion 228 of the guide catheter 226 is guided from one bodily lumen the femoral artery to the heart 200 via the inferior vena cava 210 and into a right atrium 202. In an alternative embodiment, the heart 200 can be entered from a left atrial or left ventricular side. However, such an approach is known to increase the risk of forming blood clots. The guide catheter 226 so disposed includes a proximal portion (not shown) of the guide catheter 226 remaining exposed outside of the body of the patient. Further, the guide catheter 226 is preferably configured such that the distal portion 228 is capable of being selectively angled by an operator (not shown) from outside of a body of a patient (not shown) toward the septal defect 222.

Figure 4:
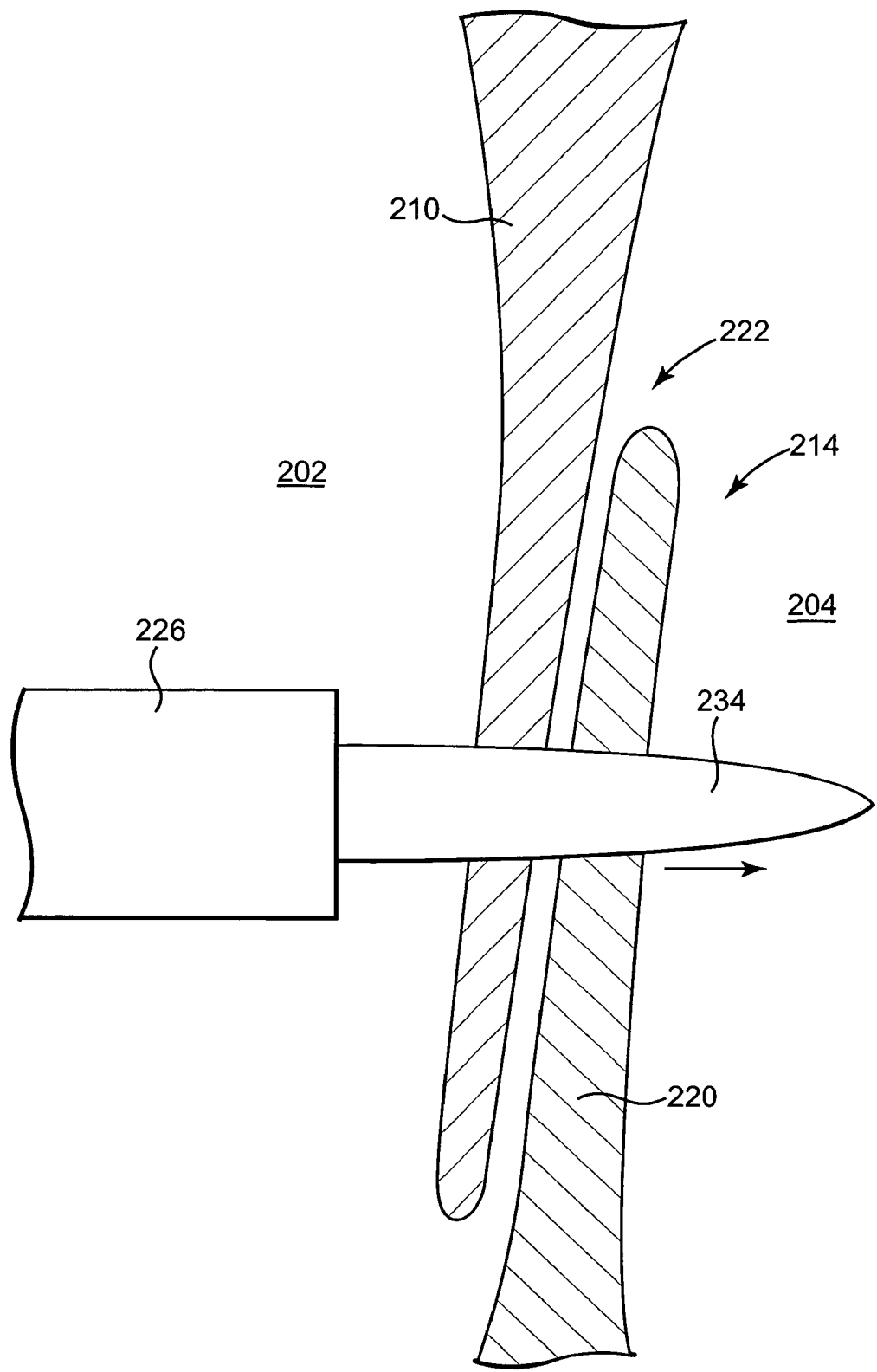

With reference to FIG. 4, one embodiment method of guiding the repair device 20 into the left atrium 204 via the guide catheter 226 includes piercing, or puncturing, the septum 214 with a transseptal needle 234. In one embodiment, the repair device 20 (hidden in FIG. 4) is guided into the left atrium 204 over the guide wire 225 (FIG. 3) through the guide catheter 226. More specifically, once the guide catheter 226 and guide wire 225 have been disposed within the right atrium 202, the repair device 20 is preferably threaded over the guide wire 225, through the guide catheter 230, and into the right atrium 202. As discussed above, the second unit 30 is preferably slidably disposed within the first unit 22. In one embodiment, the guidewire 225 is then removed and replaced with the transseptal needle 234. As described above, the guide catheter 226 is angled toward the septal defect 222 in order to direct the repair device 20 and the transseptal needle 245 to the septal defect 222. In another embodiment, the repair device 20 is configured such that the repair device 20 can be selectively angled toward the septal defect 222 to guide the transseptal needle 245 proximate the septal defect 222.

Figure 5:
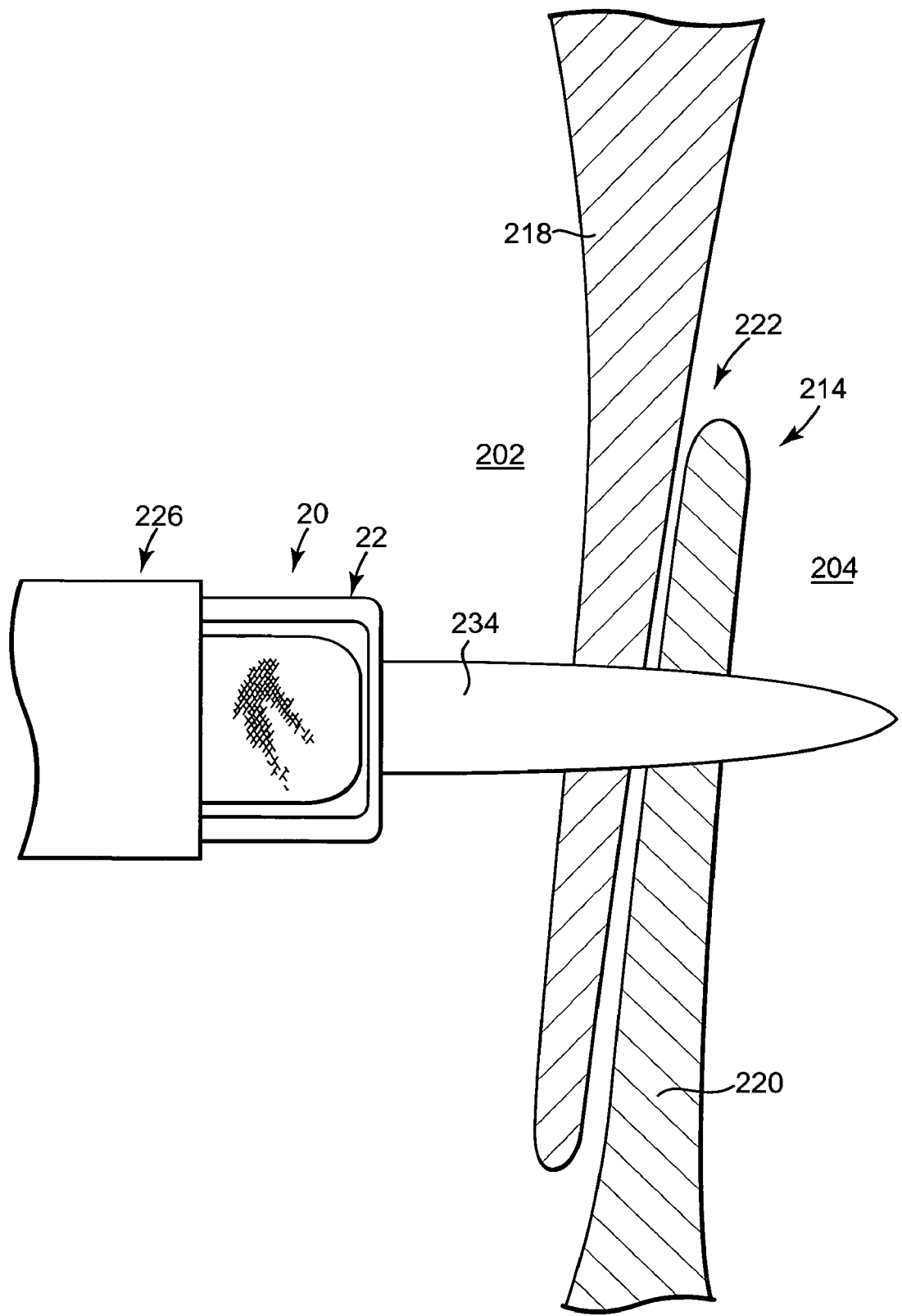

In one embodiment including an inter cardiac echo catheter, the repair device 20 is guided under inter cardiac echo to a desired position proximate the septal defect 222. In one exemplary embodiment, the desired position is proximate the septum primum 218. Once properly positioned, the transseptal needle 234 is used to puncture the atrial septum 214. In one embodiment, the septal tissue defining the septum primum 218 and the septum secundum 220 is punctured. Once the septal tissue defining the atrial septum 214 has been punctured, the transseptal needle 234 extends between the right atrium 202 and the left atrium 204. The repair unit 20 is extended from the guide catheter 226 and over the transseptal needle 234 as shown in FIG. 5. The transseptal needle 234 is removed from the repair device 20 and out of the body of the patient (not shown).

Figure 6:
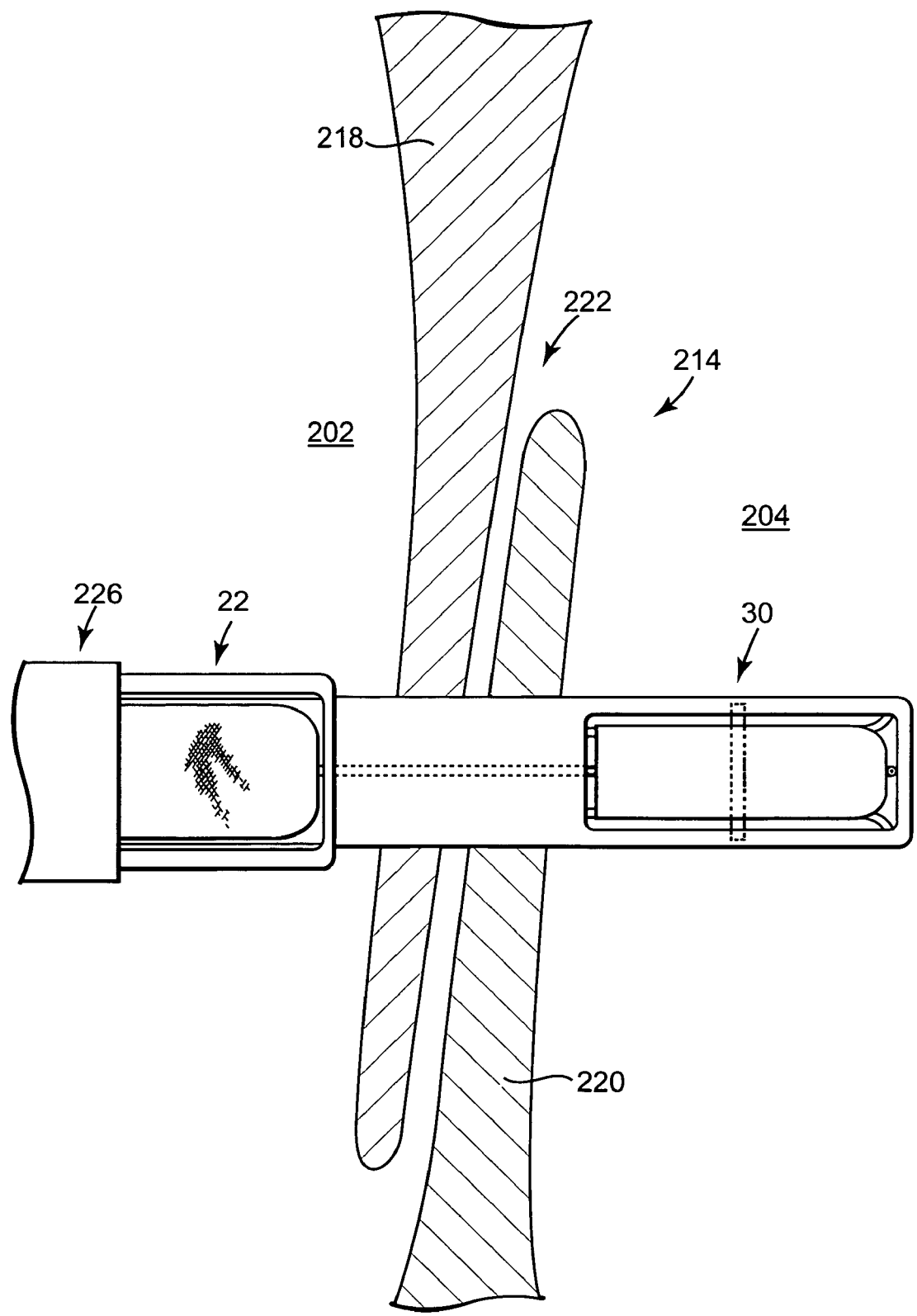

With reference from FIG. 5 to FIG. 6, the second unit 30 is preferably sufficiently advanced into the left atrium 204 such that the second unit 30 can transition to the expanded state. Once the second unit 30 has been sufficiently advanced, the transseptal needle 234 (not shown) can be removed from the repair device 20 and taken completely out of the patient (not shown).

Other methods of guiding the repair device 20 from the right atrium 202 to the left atrium 204 can also be employed. Another embodiment method of delivering the repair device 20 from the right atrium 202 to the left atrium 204 includes removing the guide wire 225 from the guide catheter 226 and inserting a transseptal needle 234 into the guide catheter 226 prior to inserting the repair device 20 into the guide catheter 226. In particular, the transseptal needle 234 is guided to the atrial septum 214 proximate the septal defect 222. The transseptal needle 234 is then used to puncture the atrial septum 214, and in one embodiment, the septum primum 218 and septum secundum 220. The guide catheter 226 can then be guided over the transseptal needle 234 into the left atrium 204. The transseptal needle 234 is removed from the guide catheter 226 and replaced with the repair device 20. The repair device 20 can then be delivered into the left atrium 204 via the guide catheter 226. In another embodiment method of guiding the repair device 20 into the right atrium 202, the atrial septum 214 is punctured with a suitably configured tip of the guide catheter 226, or alternatively, the repair device 20, to deliver the repair device 20 to the left atrium 204. In yet another embodiment, the guide catheter 226 is guided through the septal defect 222 itself to the left atrium 204 without puncturing the atrial septum 214. In another embodiment, the repair device 20 is guided through the septal defect 222 between the atria 202,204 (i.e., the septum 214 is not initially punctured).

Figure 7:
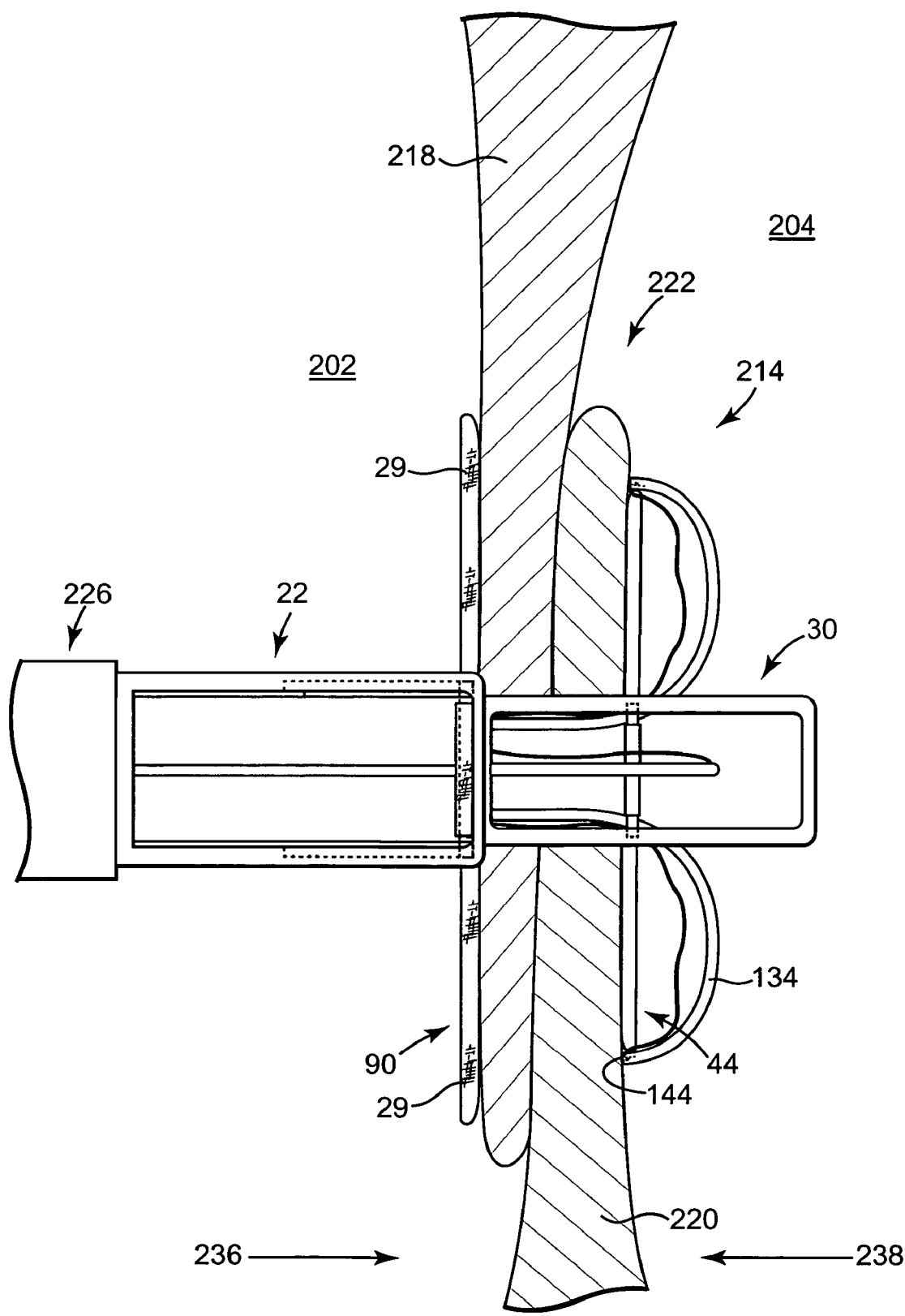

With reference to FIG. 7, in one embodiment method, when the second unit 30 is appropriate disposed in the left atrium 204, it is then expanded to the expanded state. The first unit 22 is also sufficiently extended from the guide catheter 226 and transitioned to the expanded state. The first unit 22 and the second unit 30 are then opposingly contacted with a first side 236 and a second side 238 the septum 214. In particular, the plurality of guide bodies 90 is pulled against the second side 238 of the septum 214 while the plurality of projections 44 is pushed against the first side 236 of the septum 214. In one embodiment, the second unit 30, and in particular the body proximal end 84 (not shown) is pulled back, or moved proximally, in order to make contact with the atrial septum 214 while the first unit body proximal end 40 (not shown) is pushed from outside the patient (not shown). In one embodiment, and as shown in FIG. 7, the plurality of guide bodies 90 is abutted against the septum secundum 220 and the plurality of projections 44 are contacted with the septum primum 218. Thus, the two units 22,30 are opposingly contacted with the septum 214. With this opposing contact, the first unit 22 and the second unit 30 press portions of the atrial septum 214 proximate the septal defect 222 to press or perhaps anchor or lock the atrial septum 214 in place between the two units 22,30 of the repair device 20.

As mentioned above, in one embodiment, the second unit 30 is prevented from rotating within the first unit 20. Along these lines, the generally rectangular cross-sections of both the first and second units 22,30 can act to prevent relative rotation of the two units 22, 30. With this configuration, the plurality of projections 44 of the first unit 22 in the plurality of guide bodies 90 of the second unit 30 are maintained in an aligned position. Particularly, each one of the plurality of projections 44 residing on one side of the septum 214 is aligned to a corresponding one of the plurality of guide bodies 90 residing on the opposite side of the septum 214. In one embodiment, the alignment of the plurality of guide bodies 90 with the plurality of projections 44 results in each one of the plurality of push wire assemblies 132, and in particular, the needle catheter distal end 144 being aligned with the suture receiving portion 29 defined, or otherwise included, by each one of the plurality of projections 44.

Figure 8:
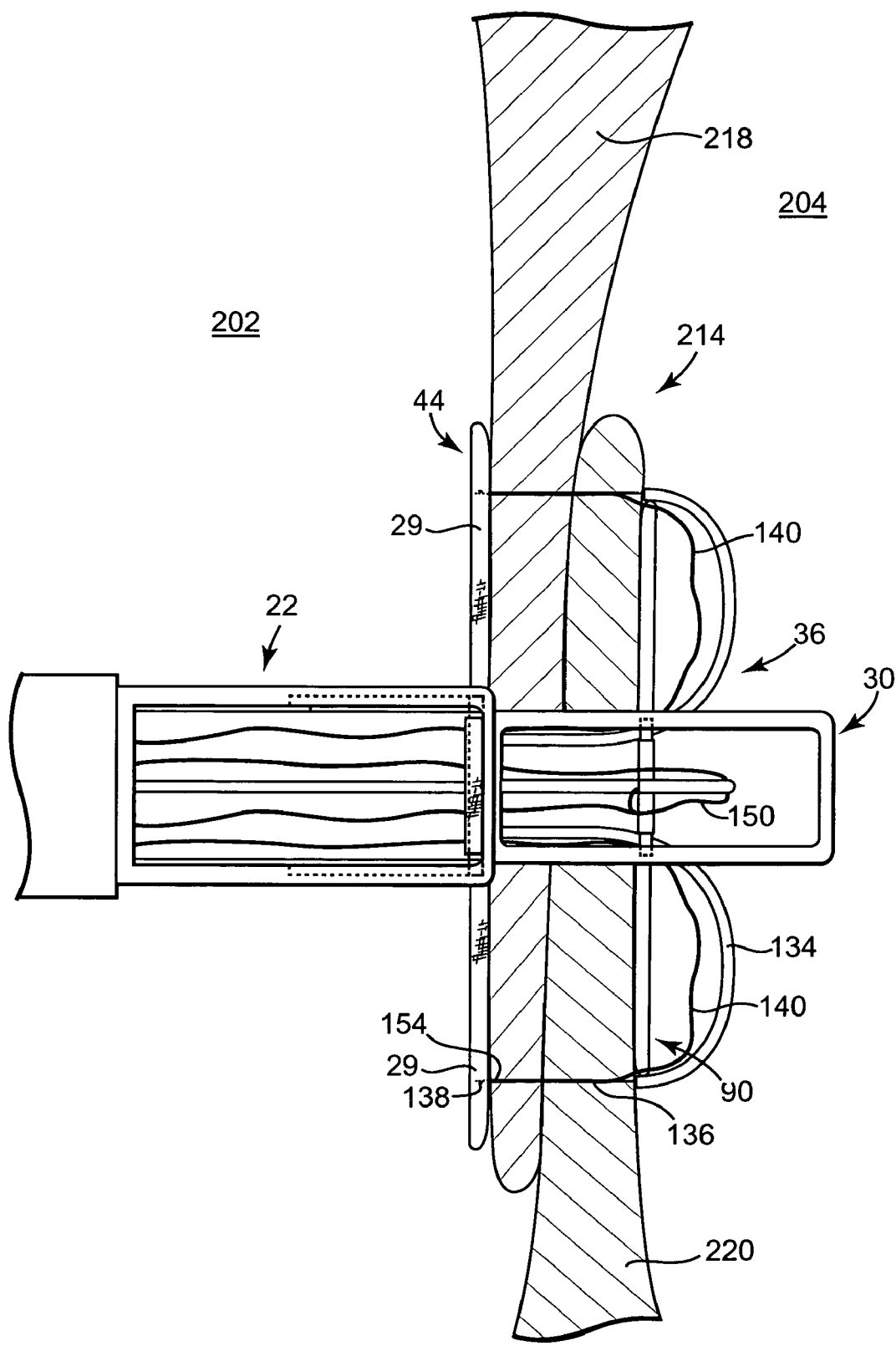

With reference to FIG. 8, the suture delivering portion 36 is then used to drive the suture 140 through the atrial septum 214 at a first location proximate the septal defect 222. In one embodiment, the push member 136 is manipulated from outside of the patient (not shown) in a distal direction to extend from the needle catheter 134. In other words, each push member 136 is pushed distally such that the needle 138 affixed to the corresponding push member 136 extends from the corresponding needle catheter 134 and is driven through the atrial septum 214, and in particular the tissue defining the atrial septum 214, with the suture first end 154 in tow. In one embodiment, both the septums primum and secundum 218, 220, are fully pierced with the first end 154 of the suture 140 in tow. As shown, the needles 138 are pushed through the atrial septum 214 and into the suture receiving portion 29 of the first unit 22 to be captured or retained therein. As shown in FIG. 8, the suture receiving portion 29 includes one of the plurality of projections 44 being formed of wire mesh such that when the barb 152 of the needle 138 is passed into the mesh, the needle 138 is anchored therein.

Figure 9:
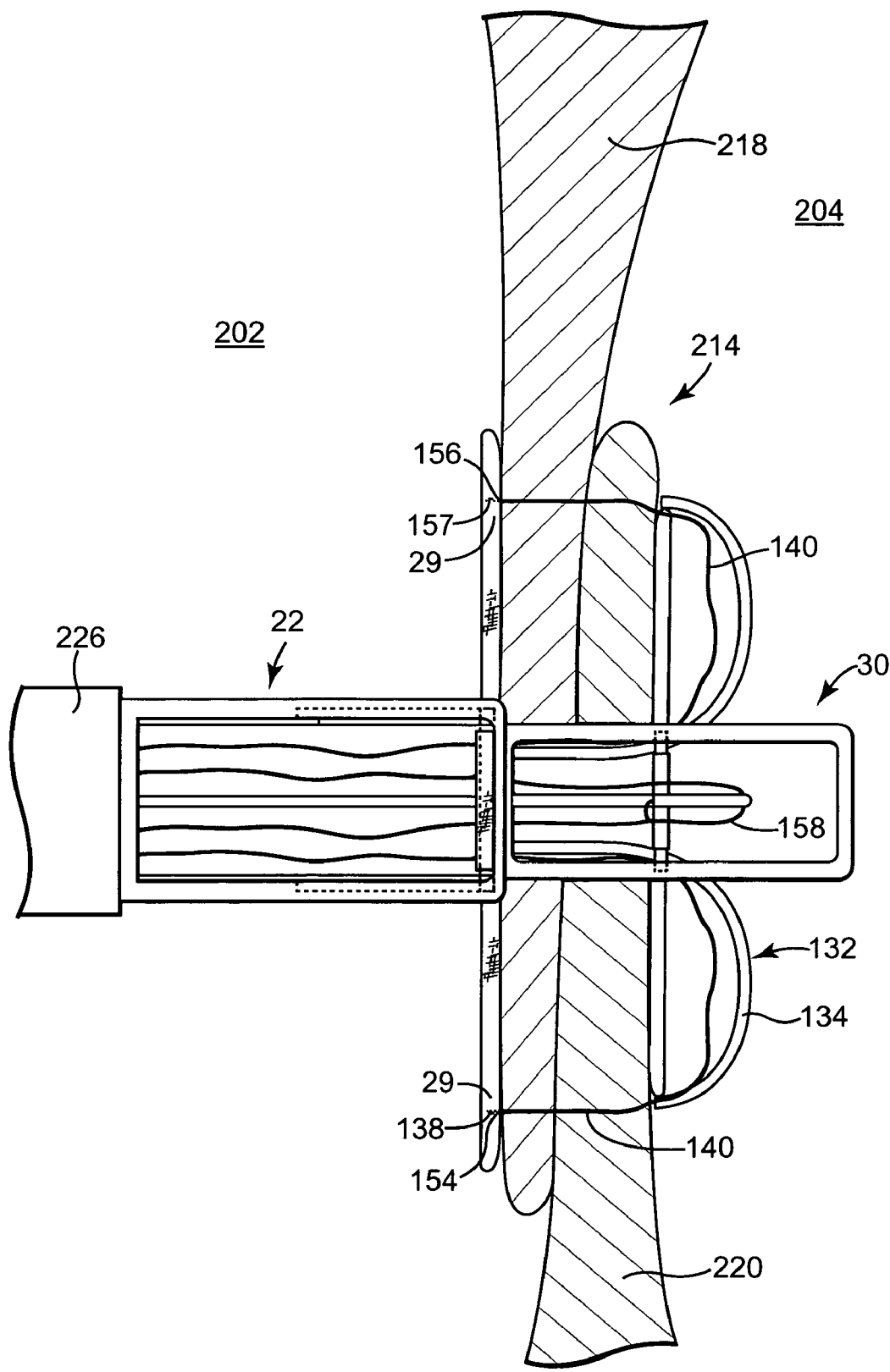

With reference to FIG. 9, the push members 136 (not shown) are then pulled, or moved, proximally from outside the patient (not shown) in order to retract the push members 136 back into the corresponding needle catheter 134. As mentioned above, the needle 138 is preferably removably affixed to the corresponding push member 136, such that pulling, or proximal movement of the push member 136 results in separation of the push member 136 from the needle 138. With the needle 138 captured by the suture receiving portion 29 of the first unit 22, along with the suture first end 154, the push member 136 is then removed from the atrial septum 214 and back into the needle catheter 134. As shown, the second end 156 of the suture 140 affixed to the second needle 157, is driven through the tissue at a second location and anchored, or captured within the suture receiving portion 29 of the first unit 22 in a similar manner. As will be described below, the two ends 154,156 can then be tied together once the first unit 22 is removed from the body of the patient (not shown) with the ends 154,156 in tow. In one embodiment, needles affixed to two ends of a second suture 158 are also driven through the tissue of the atrial septum 214 at a third and a fourth location proximate the septal defect 222 and into other ones of the plurality of projections 44 in a similar manner. It should be understood that embodiments of the method generally include a plurality of sutures being driven through the atrial septum 214 such that a first end and a second end of each of the plurality of sutures is captured by the suture receiving portion 29.

In one embodiment, once the suture 140 and second suture 158 have been captured by the first unit 22, the second unit 30 is transitioned back to the collapsed state. Following transitioning, the second unit 30 is retracted from the left atrium 204 and back within the first unit 22. In one embodiment, a hole remains where the septum 214 was punctured upon retrieval of the second unit 30 from the left atrium 204. In another embodiment, the natural elasticity of the septum 214 causes the hole to contract such that it is substantially closed.

Figure 10:
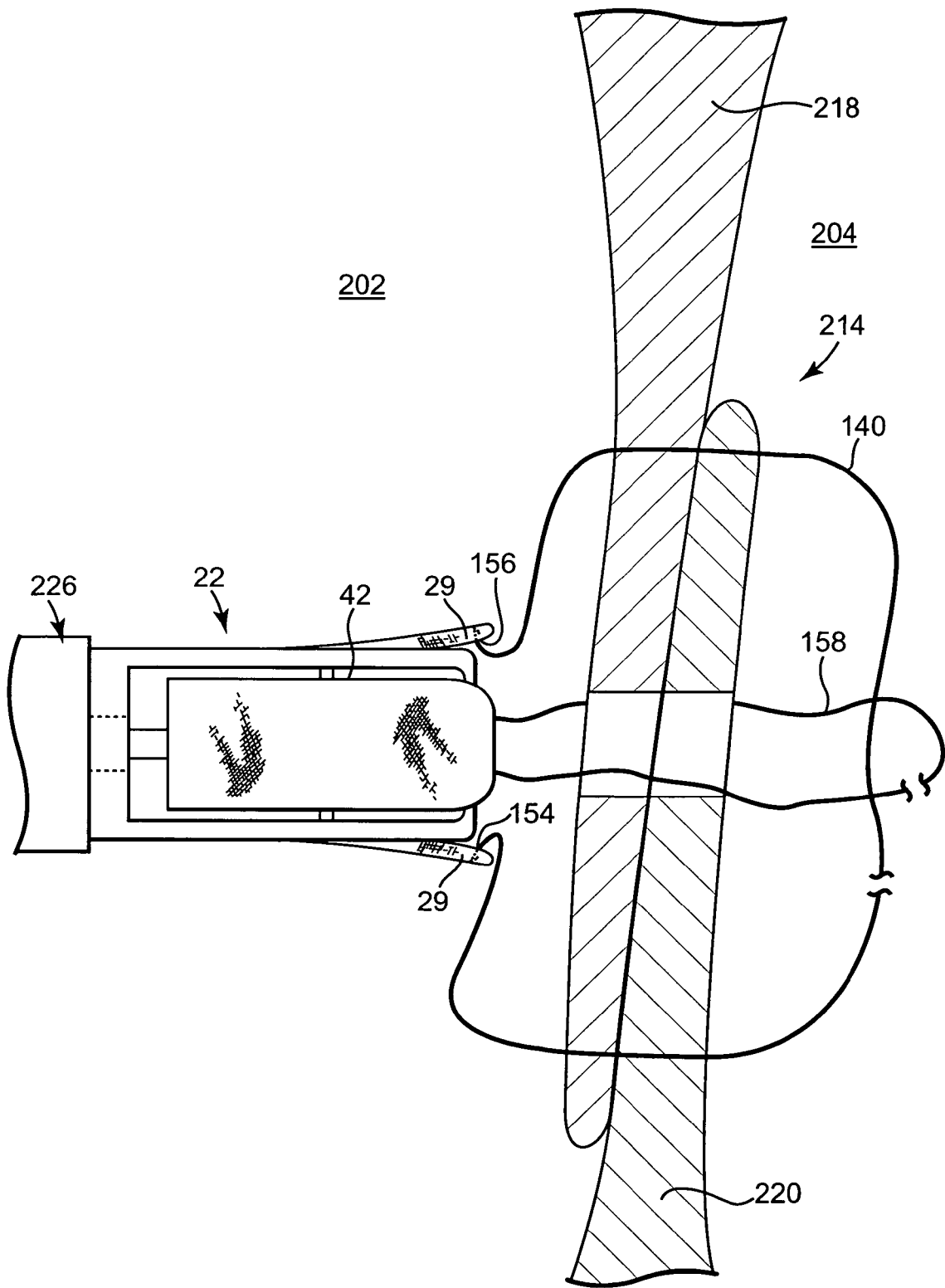

In FIG. 10, the second unit 30 (hidden) has been retracted into the first unit 22. The first unit 22 also transitions back to the collapsed state once the sutures 140, 158 have been captured. In one embodiment, the first end 154 and the second end 156 of the suture 140, and the first and second ends of the second suture 158 are drawn toward the central axis X (FIG. 1A) of the repair device 20 and into the plurality of nests 42.

Figure 11:
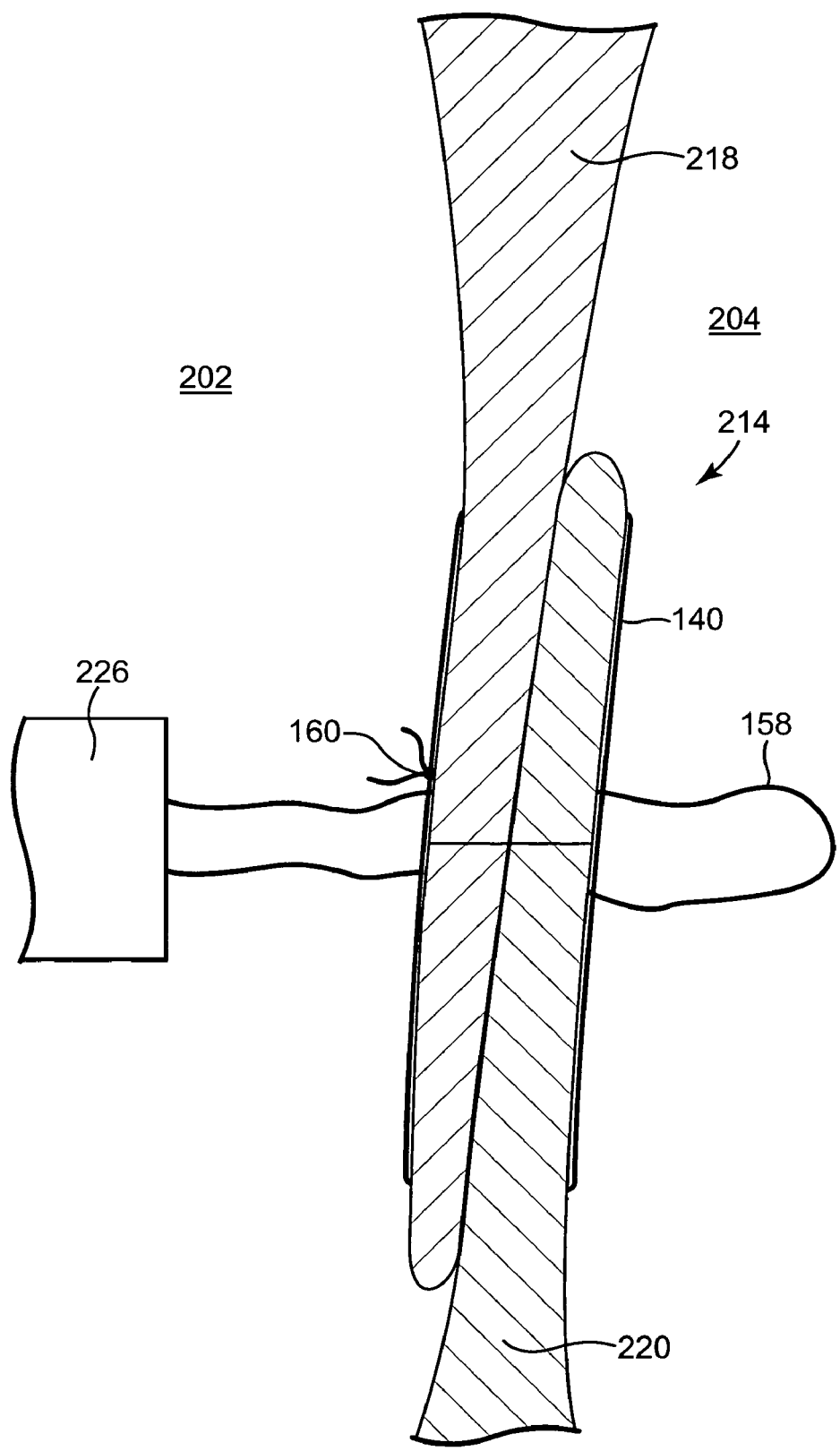

With reference to FIG. 11, the first unit 22 is retracted from the right atrium 202 and into the guide catheter 226 with the first and second ends 154,156 of the suture 140 and the first and second ends of the second suture 158 in tow. In this manner, an operator (not shown) can access the ends of the sutures 156,158 from outside of the body of the patient (not shown). As shown in FIG. 11, the two ends 156,158 can then be tied into a first knot 160, such as a simple suture. In one embodiment, a knot pusher (not shown) is used to push the first knot 160 formed in the suture 140 outside of the body of the patient back through the guide catheter 226 and to the atrial septum 214. The excess material of the suture 140 surrounding the first knot 160 can then be clipped. In one embodiment, the knot pusher includes a clipping mechanism (not shown). A similar method can be used to tie a knot 162 (FIG. 12A) in the second suture 158. As shown, the hole punctured in the septum 214 is at least partially closed with the knot 162 adjacent the septum 214.

Figure 12A:
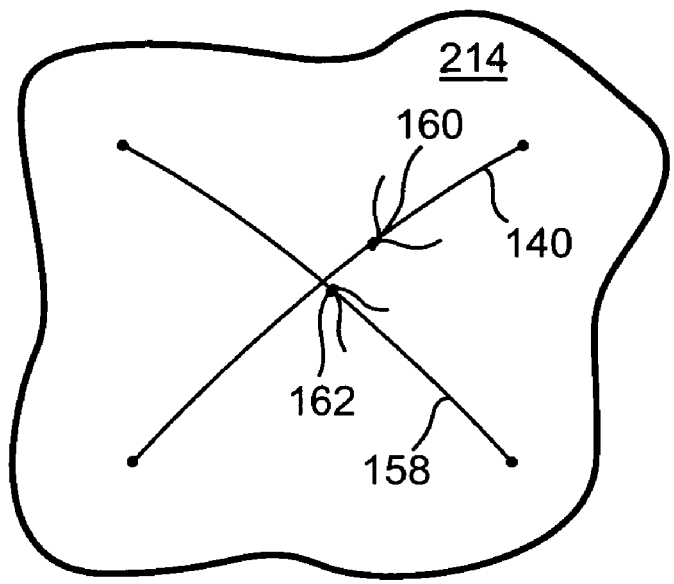
Figure 12B:
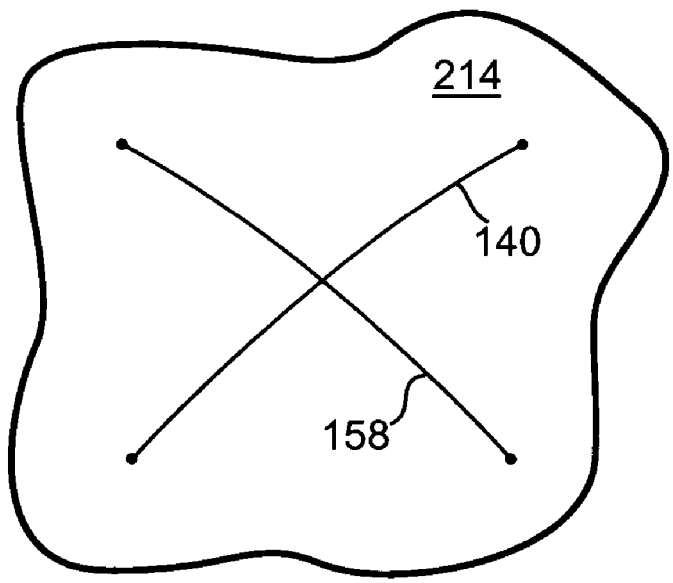

With reference to FIGS. 12A and 12B, a preferred configuration of the sutures 140, 158 and their corresponding knots 160,162 can be described. In particular, FIG. 12A shows one preferred configuration from a viewpoint of the right atrium 202. Conversely, FIG. 12B shows a preferred configuration from a viewpoint of the left atrium 204. As shown, the two sutures 140,158 act to maintain the atrial septum 214 in a closed position in order to repair the septal defect 222 (not shown). Furthermore, in one embodiment, the hole punctured in the septum is also drawn closed by the two sutures 140,158. In another embodiment, the sutures 140,158 can be used to repair a hole through the ventricular septum 216 (not shown). In another alternative embodiment, a patch (not shown) of a type known in the art can be sutured to one side of the septum 214, or two patches can be sutured to opposing sides of the septum 214, respectively. Regardless, the patch or patches can be secured by one or both of the sutures 140 or 158 in conjunction with the above method, or can be affixed separately.

As alluded to above, alternative embodiments also include additional sutures and/or patches used to repair septal defects. For example, a patch (not shown) could be delivered via the repair device 20 to the area approximate the septal defect 222 and sutured thereto utilizing an embodiment method of the present invention. Additionally, another embodiment of the present invention can include suturing an occlusion device proximate a septal defect. Furthermore, alternative suture configurations, including non-crossed configurations as otherwise shown in FIGS. 12A and 12B, are also incorporated in alternative embodiments. It is also to be understood that in one exemplary embodiment wherein the first unit 22 includes a suture delivering portion and the second unit 30 includes a suture receiving portion, the views of FIGS. 12A and 12B can be reversed such that FIG. 12A would show a view from the left atrium 204.

Figure 13A:
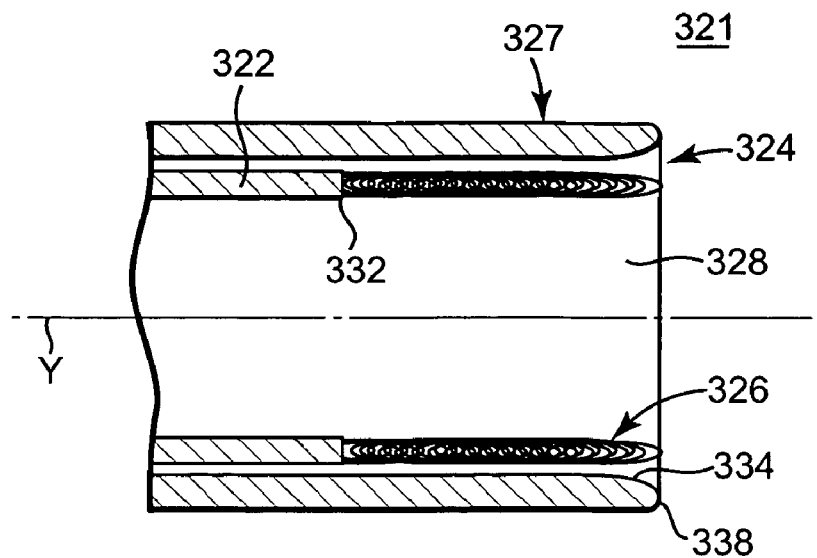
FIG. 13A is a cross-sectional view along a central axis Y of another embodiment first unit of a repair device in accordance with the present invention.
Figure 13B:
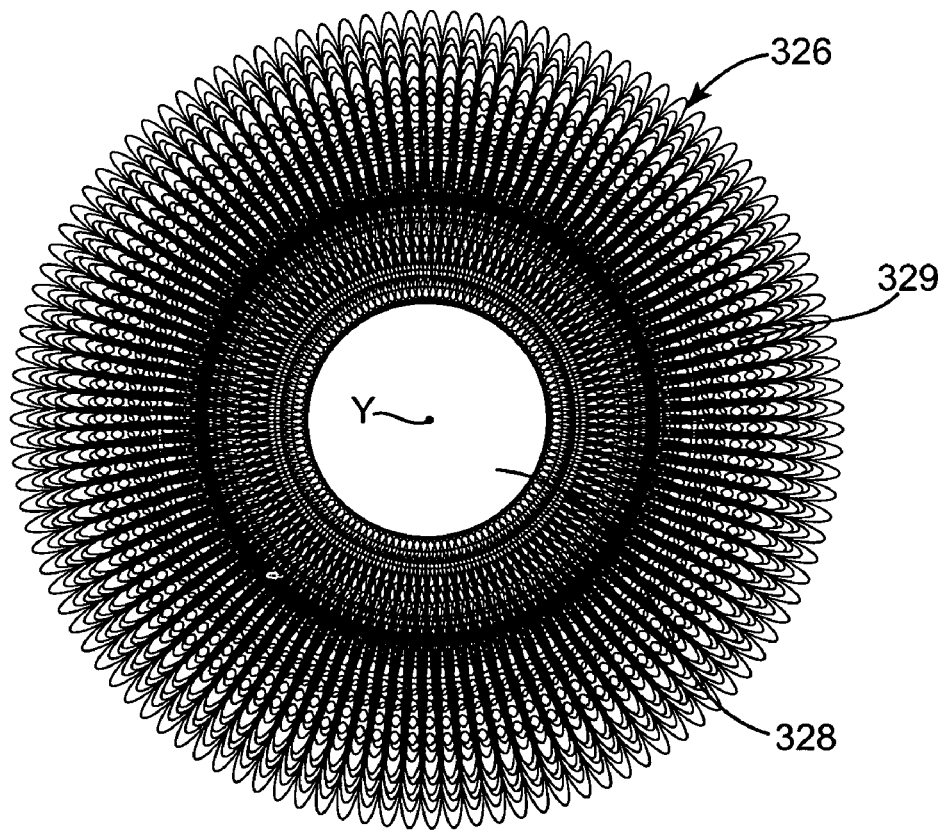
FIG. 13B is an end view of the alternative embodiment of FIG. 13A.

Although specific embodiments have been illustrated and described herein, it will be appreciated by those of ordinary skill in the art that a variety of alternate and/or equivalent implementations may be substituted for the specific embodiments shown and described without departing from the scope of the present invention. For example, FIGS. 13A and 13B illustrate an alternative embodiment first unit 321 of a repair device 320 in accordance with the present invention. Generally, the first unit 321 comprises a body 322 and an expansion assembly 324. In particular, the expansion assembly 324 includes a mesh hood 326 and an actuation catheter 327.

The body 322 is preferably formed of materials similar to those known in the art. In one embodiment, the body 322 is a catheter and defines a generally circular transverse cross-section forming an inner lumen 328. The body 322 extends from a proximal end (not shown) to a distal end 332. Further, the body 322 defines a length sufficient to allow manipulation of the proximal end while the distal end 332 is proximate a septal defect (not shown). In one embodiment, the body 322 is configured for insertion into the actuation catheter 327.

The actuation catheter 327 of the expansion assembly 324 can be a catheter of a type generally known in the art. Generally the actuation catheter 327 defines an inner lumen 334, a proximal end (not shown) and a distal end 338. As described above, the inner lumen 334 is preferably configured to accept the body 322. Additionally, the actuation catheter 327 preferably extends a length sufficient to allow manipulation of the proximal end from outside the body of the patient (not shown) while the distal end 338 is disposed proximate a septal defect (not shown).

As shown in FIG. 13A, the hood 326 is affixed to the body 322. The hood 326 is preferably configured to expand outwardly from a central longitudinal axis Y of the first unit 321 when unconstrained by the actuation catheter 327. In particular, the hood 326 can be formed of Nitinol® mesh, or another metal capable of incorporating a spring action. Alternatively, the hood 326 can be formed of expandable plastic structure. Preferably a spring action allows the hood 326 to spring between a configuration substantially perpendicular to the central longitudinal axis Y (FIG. 13B) to a configuration substantially parallel to the central longitudinal axis Y (FIG. 13A). Additionally, the hood 326 is also configured to define a suture receiving portion 329 of the repair device 320. In particular, a thickness of the hood 326 is configured to retain a first end of a suture (not shown).

As such, assembly of the body 322 and actuation catheter 327 can be described as follows. The hood 326 is affixed to the distal end 332 of the body 322. Preferably, both the body 322 and the hood 327 affixed thereto are slidably disposed within the inner lumen 334 of the actuation catheter 327.

A method of transitioning the first unit 321 to an expanded state includes sliding the body 322 and the actuation catheter 327 relative to one another such that the hood 326 is exposed from the distal end 338 of the actuation catheter 324. The spring action of the hood 327 causes the hood 327 to transition to a configuration substantially perpendicular to the central longitudinal axis Y (FIG. 13B). Another alternative embodiment a repair device further comprises a second unit substantially similar to the first unit 321, but configured to be slidably disposed within the first unit 321. In another embodiment, the second unit is substantially similar to the second unit 30 of the repair device 20.

Figure 14:
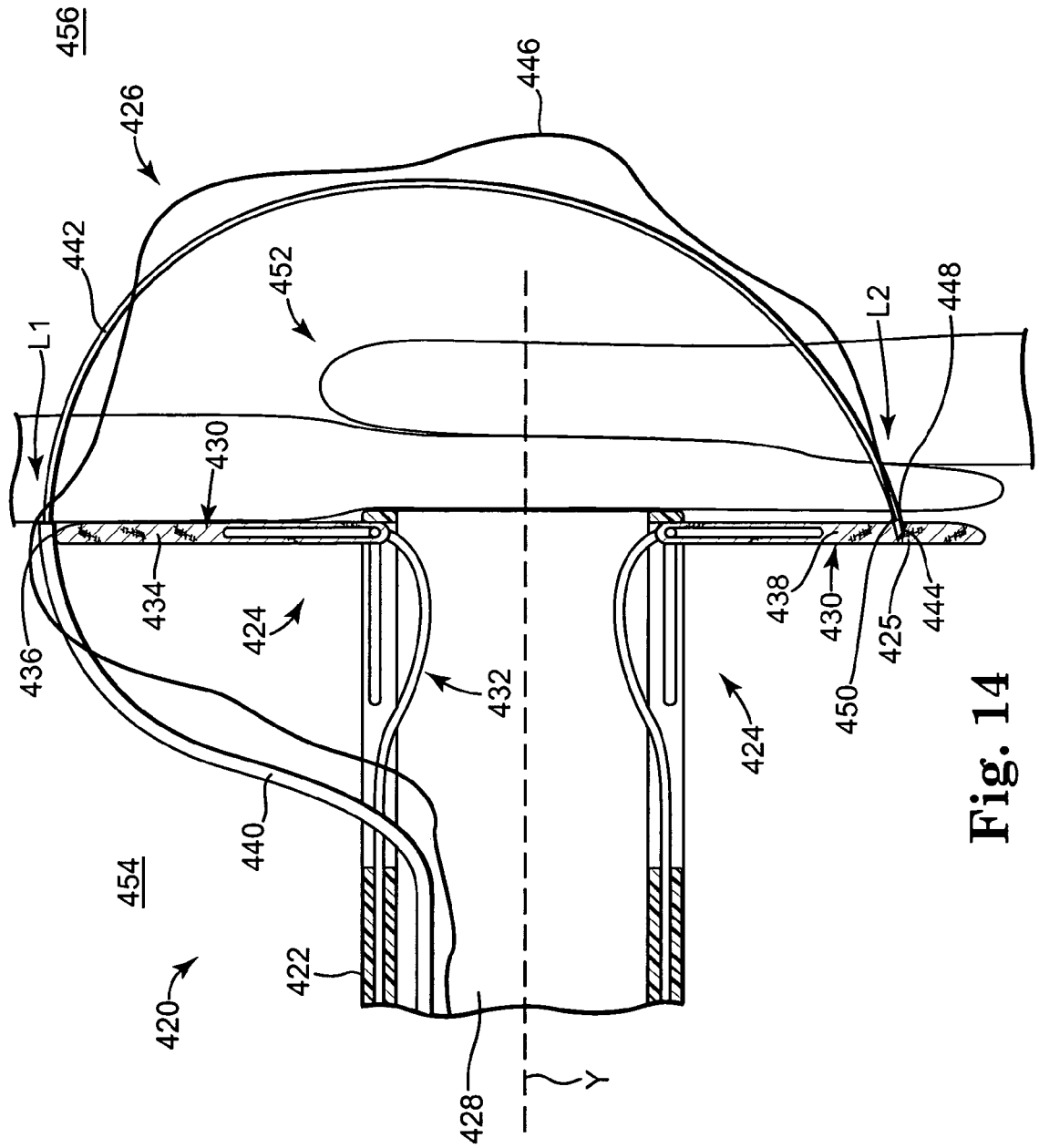
FIG. 14 is a cross-sectional view along a central axis Y of yet another embodiment repair device in accordance with the present invention.

Another alternative embodiment repair device 420 in accordance with the present invention is shown in FIG. 14. Generally, the repair device 420 includes a body 422, an expansion assembly 424, a suture receiving portion 425, and a suture delivering portion 426.

The body 422 can be formed of materials similar to those be used in association with catheters known in the art. The body 422 is configured to be coaxially received within an inner lumen of a guide catheter (not shown). The body 422 also defines a central lumen 428 of the repair device 420.

The expansion assembly 424 can be described as similar to those previously described in association with other embodiments. Generally, the expansion assembly can include a plurality of projections 430 that can be actuated with actuation wires 432. In the embodiment, the repair device 420 includes two projections 430, a first one 434 formed of a solid material and configured such that a distal end 436 of the first one 434 can be affixed to the suture delivery portion 426. A second one 438 of the plurality of projections 430 can be formed of a wire mesh material to define the suture receiving portion 425 of the repair device.

The suture delivering portion 426 of the repair device 420 can include a needle catheter 440, a push member 442, a suture needle 444, and a suture 446. The needle catheter 440 is configured to slidably accept the push member 442 within an inner lumen (not shown) of the needle catheter 440.

The push member 442 is configured to transition to adopt a curvilinear shape upon extension from the needle catheter 440. In particular, the push member 442 can be made of a shape memory metal, such as Nitinol®, with a naturally occurring curve resulting in the push member when it is unconstrained by the needle catheter 440.

The suture needle 444 and the suture 446 can be largely similar to those previously described. As such, the suture needle 444 can be removably affixed to the push member 442 at a distal end 448 of the push member 442. In another embodiment, the suture needle 444 is configured to transition to adopt a curvilinear shape upon extension from the needle catheter 440. In the embodiment shown, the suture 446, and in particular, a first end 450 of the suture 446 is affixed to the suture needle 444. In another embodiment, the first end 450 is removably affixed to the suture needle 444.

In one embodiment, the needle catheter 440 is affixed to the first one 434 of the plurality of projections 430, such that when the plurality of projections 430 are transitioned to an expanded state and abutted against a septum 452 the suture needle is positioned at a first location L1 proximate a septal defect 410.

In a related embodiment, the repair device 420 further includes a second unit (not shown) similar to that of the first unit 321 of the repair device 320. The repair device 420 can also include a second unit (not shown) similar to the first unit 22 or the second unit 30 of the repair device 22. With the addition of the second unit to the repair device 420, the septum (not shown) can be anchored between the expansion assembly 424 and the second unit to facilitate suturing in a manner similar to that described above in association with other embodiments.

As such, a method of repairing a septal defect includes expanding the plurality of projections 430 to an expanded state and abutting the plurality of projections against a first side 454 of the septum 452, such that the suture needle 444 is positioned at a first location proximate the septal defect 410. The suture needle 444, with the first end 450 of the suture 446 affixed thereto, is extended from the needle catheter 440 by actuating the push member 442 from a location outside of the patient (not shown). As the suture needle 444 is extended from the needle catheter 440, the suture needle 444 is driven through the septal tissue at the first location from the first side 454 to a second side 456 of the septum 452. As shown in FIG. 14, the push member 442 extends in a curvilinear manner as it is extended further from the needle catheter 440 until the suture needle 444 is positioned at a second location L2 proximate the septal defect 410 and driven through the tissue of the septum 452 from the second side 456 to the first side 454 and into the suture receiving portion 425.

The suture needle 444 is received within the receiving portion 425, and upon retraction of the push member 442 back into the needle catheter 440, remains captured therein with the first end 450 of the suture 446 affixed thereto and also captured accordingly. In an alternative embodiment including the first end 450 being removably affixed to the suture needle 444, the suture needle remains affixed to the push member 442 while the first end 450 of the suture 446 is captured within the capture portion 425 upon retraction of the push member 442. The expansion assembly 424 can then be transitioned back to the collapsed state and retracted from the patient with the first end 450 of the suture 446 in tow. In this manner, an operator can thereby tie the first end 450 of the suture 446 and a second end (not shown) of the suture 446 in order to repair the septal defect 410, or alternatively suture a patch thereto, for example.

As mentioned above, alternative embodiment repair devices can also include a balloon as an expansion means for either a first unit or a second unit of the alternative embodiment repair device. For example, in one embodiment, the repair device includes a balloon mounted on a catheter. In particular, the balloon can define a generally hourglass shape in an expanded state, such that the balloon can anchor septal tissue proximate a septal defect between two opposing hourglass portions of the balloon. With the alternative embodiment, a suture delivering portion similar to that described above is mounted on one hourglass portion of the balloon while a suture receiving portion is mounted on the opposite hourglass portion of the balloon. In one embodiment, the suture receiving portion includes a plurality of funnels defining a generally conical shape and having a porous material at a base of each of the funnels. The plurality of funnels is radially disposed about the one hourglass portion of the balloon with a plurality of push wire assemblies disposed about the opposite hourglass portion of the balloon. The plurality of funnels and the plurality of push wire assemblies are aligned with one another such that a plurality of needles affixed to a plurality of suture ends can be extended from each of the plurality of push wire assemblies into each of the plurality of funnels following expansion of the balloon.

As such, one embodiment method of repairing a septal defect utilizing the alternative embodiment repair device can include the following: guiding the repair device to an area approximate a septal defect; guiding the repair device through the septum; expanding the balloon of the repair device to the expanded state to press the septum; actuating the suture delivering portion to drive a plurality of suture ends through the tissue defining the septum and into the suture receiving portion of the repair device; transitioning the balloon back to a collapsed state; retracting the repair device form the body with a plurality of suture ends in tow; and tying the plurality of suture ends.

Additionally, alternative sewing assemblies, such as, for example, a repeating mechanical sewing machine are also included within the scope of the present invention. For example, in another alternative embodiment, a repeating mechanical sewing machine includes a first unit acting analogously to a bottom mechanism of a sewing machine with a second unit including a needle pusher acting analogously to a needle driving portion of a sewing machine. In one embodiment, the two units are configured to be rotated in concert while aligned on opposing sides of a septal defect. As the two units are rotated, the needle pusher repeatedly drives a needle that is carrying a portion of a suture through the septum and to the first unit such that the suture is continuously and repeatedly driven through the septum at various locations proximate the septal defect. In this manner, the suture can then be "tightened up" and the septal defect sewn shut.

In light of the above, an improved manner of repairing congenital defects via less invasive means, including repairing those defects not amenable to the use of occlusion devices, is presented herein. In particular, those of ordinary skill in the art will understand the text above and accompanying figures to present a method and apparatus capable of allowing a surgeon to suture septal tissue proximate a septal defect with less invasive methods than those related to accessing the heart through the chest of a patient. This application is intended to cover any adaptations or variations of the specific embodiments discussed herein. As such, it is intended that this invention be limited only by the claims and the equivalents thereof.

What is claimed is:

1. A method of repairing a septal defect in a septum defined by septal tissue, the method comprising:
   introducing a guiding catheter into a bodily lumen of a patient;
   delivering a repair device proximate the septal defect via the guiding catheter, wherein
     the repair device includes,
       a suture delivering portion maintaining a suture, and
       a suture receiving portion;
   positioning the suture at a first location proximate the septal defect with the repair device;
   positioning the suture at a second location proximate the septal defect and spaced from the first location with the repair device;
   pressing overlapping tissue segments of the septum together and into contact with one another with the repair device by applying a first force to a first side of the septum and applying a second force to a second side of the septum opposite the first side;
   driving the suture through the septal tissue at the first location with the repair device after the step of applying the first and second forces;
   driving the suture through the septal tissue at the second location with the repair device after the step of applying the first and second forces;
   capturing the suture with the repair device; and
   tying the suture.

2. The method of claim 1, wherein the suture is captured with the suture receiving portion after the suture has been driven through the septal tissue.

3. The method of claim 1, further comprising:
   positioning a second suture at a third location proximate the septal defect with the repair device, wherein the second suture is maintained by the suture delivering portion;
   driving the second suture through the septal tissue at the third location with the repair device;
   positioning the second suture at a fourth location proximate the septal defect with the repair device;
   driving the second suture through the septal tissue at the fourth location with the repair device;
   capturing the second suture with the repair device; and
   tying the second suture.

4. The method of claim 1, wherein capturing the suture with the repair device includes, capturing the suture within a mesh material of the suture receiving portion.

5. The method of claim 1, wherein capturing the suture with the repair device includes, capturing the suture within a porous material of the suture receiving portion.

6. The method of claim 1, wherein capturing the suture with the repair device includes, capturing the suture by magnetic attraction with the suture receiving portion.

7. The method of claim 1, wherein capturing the suture with the repair device includes, capturing the suture by frictional engagement with the suture receiving portion.

8. The method of claim 1, wherein the septum is the atrial septum and the septal defect is a defect in the atrial septum.

9. The method of claim 1, wherein the septal defect is a patent foramen ovale.

10. The method of claim 1, wherein the septum is the ventricular septum and the septal defect is a defect in the ventricular septum.

11. The method of claim 1, wherein positioning the suture at the first location with the repair device includes:
    positioning a first end of the suture at the first location proximate the septal defect;
    wherein driving the suture through the tissue at the first location with the repair device includes:
      driving the first end of the suture from the second side of the septum to the first side of the septum with the suture delivering portion;
    wherein positioning the suture at the second location with the repair device includes:
      positioning a second end of the suture at the second location proximate the septal defect;
    wherein driving the suture through the tissue at the second location with the repair device includes:
      driving the second end of the suture from the second side of the septum to the first side of the septum with the suture delivering portion; and
    wherein capturing the suture with the repair device includes:
      capturing the first end and the second end of the suture with the suture receiving portion at the first side of the septum.

12. The method of claim 11, wherein the repair device further includes:
    a first unit defining the suture receiving portion; and
    a second unit defining the suture delivering portion;
    wherein the first unit and the second unit are coaxially received together and both the first unit and the second unit are coaxially received within the guide catheter; and
    further wherein repairing a septal defect in a septum defined by septal tissue further comprises,
      delivering the first unit to the first side of the septum;
      delivering the second unit to the second side of the septum;
      positioning the suture receiving portion and suture delivering portion relative to one another such that the suture receiving portion is aligned to capture the suture as delivered by the suture delivering portion; and
      pressing the septal tissue between the first unit and the second unit.

13. The method of claim 12, further comprising:
    delivering a transseptal needle proximate the septal defect via the repair unit;
    puncturing the septum with a transseptal needle such that the needle extends between the first side of the septum and a second side of the septum; and
    guiding the second unit over the transseptal needle and through the septal tissue from the first side of the septum to the second side of the septum.

14. The method of claim 12, further comprising:
    guiding the second unit through the septal defect from the first side of the septum to the second side of the septum.

15. The method of claim 12, wherein the first end of the suture is affixed to a first suture needle and the second end of the suture is affixed to a second suture needle, and further wherein capturing the first and second ends of the suture with the suture receiving portion includes driving the first and second needles into the suture receiving portion.

16. The method of claim 11, wherein prior to the steps of driving the suture through the septal tissue, the suture is not captured by the suture receiving portion.

17. The method of claim 1, further comprising:
securing a patch across the septal defect at one side of the septum.

18. The method of claim 1, wherein:
applying a first force includes directing the first side toward the second side; and
applying a second force includes directing the second side toward the first side.

19. The method of claim 18, wherein the first and second forces are simultaneously applied to compress the first and second sides together.

20. The method of claim 1, wherein the step of pressing opposing sides of the septum occurs prior to the steps of driving the suture through the septal tissue and capturing the suture with the repair device.

21. A method of repairing a septal defect in a septum having opposing first and second sides defined by septal tissue, the method comprising:
introducing a guiding catheter into a bodily lumen of a patient;
delivering a repair device proximate the septal defect via the guiding catheter, wherein the repair device includes:
a suture delivering portion maintaining a suture having opposing, first and second ends,
a suture receiving portion;
positioning the first end of the suture at a first location proximate the septal defect with the repair device, the first location being adjacent the second side of the septum, opposite the first side of the septum;
positioning the second end of the suture at a second location proximate the septal defect with the repair device, the second location being adjacent the second side of the suture, opposite the first side of the septum, and spaced from the first location;
simultaneously pressing the opposing sides of the septum together with the repair device;
driving the first end of the suture through the septal tissue from the second side of the septum to the first side of the septum; driving the second end of the suture through the septal tissue from the second side of the septum to the first side of the septum;
wherein driving the ends of the suture occurs after the step of simultaneously pressing;
capturing the first and second ends of the suture with the repair device; and
tying the suture.

\* \* \* \* \*